US011458017B2

(12) United States Patent
Smolinsky

(10) Patent No.: US 11,458,017 B2
(45) Date of Patent: Oct. 4, 2022

(54) DEVICE AND METHOD FOR TRANSCATHETER MITRAL AND TRICUSPID VALVE REPAIR

(71) Applicant: VVITAL BIOMED LTD., Raanana (IL)

(72) Inventor: Aram Kurt Smolinsky, Netanya (IL)

(73) Assignee: VVITAL BIOMED LTD., Raanana (IL)

( * ) Notice: Subject to any disclaimer, the term of this patent is extended or adjusted under 35 U.S.C. 154(b) by 0 days.

(21) Appl. No.: 16/497,123

(22) PCT Filed: Mar. 27, 2018

(86) PCT No.: PCT/IL2018/050351
§ 371 (c)(1),
(2) Date: Sep. 24, 2019

(87) PCT Pub. No.: WO2018/178977
PCT Pub. Date: Oct. 4, 2018

(65) Prior Publication Data
US 2020/0138577 A1 May 7, 2020

Related U.S. Application Data

(60) Provisional application No. 62/608,629, filed on Dec. 21, 2017, provisional application No. 62/476,908, filed on Mar. 27, 2017.

(51) Int. Cl.
*A61F 2/24* (2006.01)
(52) U.S. Cl.
CPC ............ *A61F 2/2448* (2013.01); *A61F 2/246* (2013.01); *A61F 2/2466* (2013.01);
(Continued)

(58) Field of Classification Search
CPC .... A61F 2/2442; A61F 2/2445; A61F 2/2448; A61F 2/246
See application file for complete search history.

(56) References Cited

U.S. PATENT DOCUMENTS

| 5,061,277 A | 10/1991 | Carpentier et al. |
| 5,104,407 A | 4/1992 | Lam et al. |
| (Continued) | | |

FOREIGN PATENT DOCUMENTS

| CN | 105451686 | 3/2016 |
| EP | 3372198 | 6/2017 |
| (Continued) | | |

OTHER PUBLICATIONS

Kodali, Susheel MD, A New Transcatheter Hemi-Valve for Mitral Regurgitation: Design Concept and Preclinical Observations, Presented at TCT2018, Sep. 21, 2018.
(Continued)

*Primary Examiner* — Leslie Lopez
(74) *Attorney, Agent, or Firm* — The Roy Gross Law Firm, LLC; Roy Gross

(57) ABSTRACT

There is provided herein a supra mitral device for mitral/tricuspid valve repair in a subject in need thereof, the device comprising: a main body portion having essentially annular D-shape with an eccentric opening, such that a posterior section of said main body portion is wider than an anterior section of said main body portion, said posterior section of said main body portion configured for coverage and attachment to essentially the whole section of the posterior leaflet of the mitral valve which faces the left atrium on systole, thereby preventing and/or reducing mitral regurgitation, wherein said posterior section of said main body portion is made of a pliable material, adapted to stiffen after implantation of the device.

19 Claims, 33 Drawing Sheets

(52) U.S. Cl.
CPC .............. *A61F 2210/0014* (2013.01); *A61F 2220/0008* (2013.01); *A61F 2230/0013* (2013.01); *A61F 2230/0039* (2013.01); *A61F 2230/0091* (2013.01)

(56) References Cited

U.S. PATENT DOCUMENTS

| | | | |
|---|---|---|---|
| 5,540,701 | A | 7/1996 | Sharkey et al. |
| 6,368,348 | B1 | 4/2002 | Gabbay |
| 6,520,974 | B2 | 2/2003 | Tanner et al. |
| 6,726,716 | B2 | 4/2004 | Marquez |
| 8,382,653 | B2 | 2/2013 | Dubi et al. |
| 8,888,843 | B2 | 11/2014 | Khairkhahan et al. |
| 10,166,098 | B2 | 1/2019 | Khairkhahan et al. |
| 2005/0004668 | A1* | 1/2005 | Aklog ............... A61F 2/2448 623/2.36 |
| 2005/0010287 | A1* | 1/2005 | Macoviak ............ A61F 2/2454 623/2.36 |
| 2005/0038509 | A1* | 2/2005 | Ashe ................. A61F 2/2454 623/2.36 |
| 2005/0107871 | A1 | 5/2005 | Realyvaszuez et al. |
| 2009/0264996 | A1 | 10/2009 | Vanermen et al. |
| 2010/0030329 | A1 | 2/2010 | Frater |
| 2012/0203336 | A1* | 8/2012 | Annest ............... A61F 2/2427 623/2.36 |
| 2012/0277853 | A1 | 11/2012 | Rothstein |
| 2014/0364944 | A1* | 12/2014 | Lutter ............... A61B 17/0401 623/2.17 |
| 2015/0100115 | A1 | 4/2015 | Matheny |
| 2016/0030176 | A1 | 2/2016 | Mohl et al. |
| 2017/0189186 | A1 | 7/2017 | Mohl |
| 2017/0258589 | A1 | 9/2017 | Pham et al. |
| 2018/0256318 | A1 | 9/2018 | Khairkhahan et al. |
| 2019/0076249 | A1 | 3/2019 | Khairkhahan et al. |
| 2019/0175344 | A1 | 6/2019 | Khairkhahan |

FOREIGN PATENT DOCUMENTS

| | | |
|---|---|---|
| WO | 2015022710 | 2/2015 |
| WO | 2015052570 | 4/2015 |

OTHER PUBLICATIONS

Azeem, Latib MD Emerging New Devices for Percutaneous Transcatheter Mitral and Tricuspid Repair. Presented at Montefiore Medical Center, New York, USA (2018).

Mohl, Werner MD. Transvascular repair of mitral valve prolapse: The Mitral Butterfly, TCT Oct. 29-Nov. 2, 2016, Washington, DC (2016).

Pras, Fabiren MD (2019) Posterior Leaflet Augmentation and Restoration, TVT Jun. 12-15, 2019, Chicago, IL.

Granada, Juan F MD, Trans-Catheter Mitral Valve Intervention: the Next Interventional Revolution? Presented at Solaci CACI (Aug. 2017).

International Search Report for PCT/IL2018/050351 Completed Jul. 4, 2018; dated Jul. 4, 2018 9 Pages.

Written Opinion for PCT/IL2018/050351 Completed Jul. 4, 2018; dated Jul. 4, 2018 8 Pages.

* cited by examiner

400″

400″

400″

R. A. Levine, E. Schwammenthal: *Circulation.* 2005;112:745-758

Normal heart

Heart post posterior MI

S. Mitsuyama et al.: Mitral Valve Repair by Posterior Leaflet Augmentation for Ischemic Mitral regurgitation. In: AATS Mitral Conclave; Breakout Session 9: Surgery for Ischemic Mitral Regurgitation, Thursday, April 27, 2017

DEVICE AND METHOD FOR TRANSCATHETER MITRAL AND TRICUSPID VALVE REPAIR

RELATED APPLICATIONS

This application is a National Phase of PCT Patent Application No. PCT/IL2018/050351 having International filing date of Mar. 27, 2018, which claims the benefit of priority of U.S. Provisional Application Nos. 62/476,908 and 62/608,629 filed on Mar. 27, 2017 and Dec. 21, 2017, respectively. The contents of the above applications are all incorporated by reference as if fully set forth herein in their entirety.

TECHNICAL FIELD

The present disclosure generally relates to devices and methods for Transcatheter Atrioventricular Valves Repair or Replacement, namely the mitral and the tricuspid valves, Commonly termed Trans Catheter Mitral Valve Replacement (TMVR) or repair (TMVRr), or Per Cutaneous Mitral Valve Repair or Replacement (PCMVR).

BACKGROUND

The atrioventricular valves are one-way valves, and like their name implies, are the passage from the atria to the ventricles. On the left side of the heart, situated between the left atrium and the left ventricle is the Mitral Valve. On the right side of the heart, situated between the right atrium and right ventricle is the Tricuspid Valve. Their basic anatomy is quite similar. The mitral apparatus has three components: 1) The leaflets, which function like doors of a one-way gate that actually hold the blood from flowing back from the left ventricle to the left atrium. 2) The chordae (chords) that hold the free margin of the leaflets on one end and the heart myocardium (muscle) on the other end. 3) The papillary muscles (they are an intrinsic part of the heart muscle) which anchor the chordae to the heart muscle/myocardium. As a complete system, it resembles two half-domes of a parachute, with chords at its free margins, anchored on the papillary muscles tips (like the paratrooper in this comparison). Damage/disease of any one of the mitral valve apparatus components can prevent proper leaflet coaptation, namely mitral regurgitation (MR), also termed mitral insufficiency (MI) or mitral leak.

There are usually two major leaflets (the anterior leaflet and the posterior leaflet), that guard the opening, surrounded by the so called mitral valve annulus ("so called" because the term annulus implies a complete ring, which it is not, there is no annulus tissue at the middle of the posterior leaflet). Thus, during left ventricular systole, when the left ventricle contracts, the ensuing rise in intra-ventricular pressure fills the valve and pushes it backward (backward relates to the expected blood flow direction, also referred to as retrograde) toward the left atrium. The chordae tendineae stop the leaflets at the plane of the annulus, where the valve closes the passage from the ventricle to the left atrium, and the leaflets free margins coapt. Coaptation means that unlike a gate door, the leaflet half-domes are like a parachute—most of it facing the left atrium, the margins however dome down into the ventricle and coapt with the down doming part of the opposing leaflet. A one-way valve mechanism is thus established. During diastole, the pressure in the left ventricle drops abruptly to around zero mmHg and the pressure gradient between the atria and the ventricle reverses. Now the atrial pressure is higher than the ventricular pressure, and blood flows down the pressure gradient from the left atrium to the left ventricle, pushing the mitral leaflets toward the ventricle, thus opening the valve which facilitates blood flow into the left ventricle.

Mitral regurgitation (MR), also referred to as mitral insufficiency, mitral incompetence or mitral valve leak, is a disorder of the heart in which the mitral valve does not close properly during LV contraction, and ensuing rise in the LV pressure. Valve regurgitation means some blood flows backwards from the left ventricle, through the malfunctioning segment of the mitral valve, into the left atrium. The resultant rise in left atrial pressure causes blood congestion in the lung, whose clinical manifestation is shortness of breath on effort, up to pulmonary edema and death, a situation called congestive heart failure of varying degrees.

The etiologies of MR can be presented as two groups:
  Primary MR (also: Structural MR, Degenerative MR)
  Secondary MR (Functional MR, FMR)

Primary and secondary MR are fundamentally different diseases, which share improper leaflet coaptation, which can, however, in some situations be treated with the same technological approach. They differ in their pathophysiology, anatomy, outcomes and approaches to treatments. Whereas in degenerative MR there is an obvious structural defect, like torn chordae, severe myxomatous changes, fibro-elastic deficiency or post SBE damage; in functional MR the valve appears normal. However, MR does occur due to a dysfunction related to other components of the mitral valve apparatus: the heart muscle (myocardium). The impairment is due to an infarcted posterior wall which causes inappropriate posterior leaflet movement and, as a result, as the heart muscle is attached to the valve via the chordae, the posterior leaflet is pulled down ("Tethering of the posterior leaflet"), proper coaptation of the anterior and posterior leaflets is not achieved.

Whatever the causal factor is, degenerative of functional, proper coaptation of the leaflets is not achieved. Every valve repair device has to re-institute a good coaptation, in order to reduce/abolish the mitral leak. Also, whatever the casual factor is, the volume of the regurgitant valve becomes an addition to the basic normal full diastolic volume of the LV, which means extra volume load on the heart on each heart bit/cycle. The heart adapts to the increase in volume by slow dilatation of all chambers, both left atrium (LA) and LV, including mitral annulus dilatation as well, which generates even more MR and even more volume load on the left heart. A vicious cycle is thus established, in which occurrence of MR causes a gradual increase of the MR severity. Whatever the etiology, the valve repair device has to include prevention of further annular dilatation, or even reduction of the annular diameter. Degenerative mitral valve disease accounts nowadays for approximately 85% of the patients; however, its incidence is not expected to rise. However, functional MR is the rapidly growing segment of the mitral regurgitation population, mostly reflecting the rise in the age of the population (as much as 13% of people above 75 years have some FMR).

Procedures for mitral valve replacement and repair, which have proven to be efficient and reproducible, are employing open heart surgery. They are extremely invasive, require considerable recovery time, and in very high-risk patients may have prohibitive mortality. Per-cutaneous techniques now enable surgeons/invasive cardiologists to access cardiac valves without open-heart surgery. Catheters are inserted into vasculature at a site that is relatively distant from the heart, or directly via the heart apex. The catheters carry therapeutic devices through the patient's vasculature (or transapical) to the malfunctioning heart valve. Such per-catheter minimally invasive devices and procedures are well developed and approved for stenotic aortic valves. This technique was found not to be applicable to the regurgitant mitral valve due to the distinct differences between the calcific and stenotic aortic valves and the regurgitant mitral valves pathologic anatomy.

The many attempted projects of TMVR (Transcatheter Mitral Valve Replacement) until now have not had much success. None have received FDA approval and are far from competing with or even approaching the surgical results. In TMVRr (Transcatheter Mitral Valve Repair) one device, the MitraClip (by Abbott), is FDA approved recently and is employed. It is a transcatheter version of the surgical "Alfieri Repair" (edge to edge technique). However, the edge to edge repair was proven to be not as effective without additional annuloplasty. This may explain the limited and highly selective group of patients MitraClip is good for.

There thus remains a real unmet need for percutaneous trans-catheter techniques for repairing and/or replacing mitral valves and tricuspid valves for a large patient population which was not met until now.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, there is provided a supra mitral device for mitral/tricuspid valve repair, the supra mitral device having an essentially annular shape—D shape and having an opening (e.g., an eccentric opening), such that the width of the posterior section of the supra mitral device is essentially the same as the amplitude/height of the section of the posterior mitral leaflet which faces the left atrium on systole, while the width of the anterior section of the supra mitral device is thinner than the width of the posterior section (and may typically be 3-8 mm).

According to some embodiments, the supra mitral device may be used to treat primary mitral regurgitation (MR) (also called: struc+tural MR, degenerative MR).

According to additional or alternative embodiments, the supra mitral device may be used to treat secondary MR (also called: functional MR, or FMR).

According to some embodiments, the supra mitral device may be used for mitral valve repair and/or for tricuspid valve repair.

According to some embodiments, there is provided a supra mitral device having a "horse shoe" configuration or a D shape where the anterior section is partial or incomplete, such that the supra mitral device has a form of an unclosed ring (opened perimeter where the two ends of the supra mitral device are not joined), or any other shape which is configured for attachment to the posterior leaflet of the mitral valve. According to some embodiments, the two ends of the unclosed ring may be configured to overlap once positioned on the valve leaflets and optionally, to be coupled to the leaflet, thus securing the overlap of the two ends. The overlap may be anteriorly or posteriorly (namely, two layers over the middle of the posterior leaflet, the P2 segment).

According to some embodiments, the supra mitral device is configured for attachment to the leaflets of the mitral valve all around, thereby preventing and/or alleviating mitral regurgitation and/or prolapse of segments of the posterior leaflet.

According to some embodiments, attachment of the supra mitral device to the functioning leaflet of the mitral valve is a means to engage the many chordae that were not torn, via the attachment to the valve leaflet, to support the flailing segment. According to some embodiments, supra mitral device attachment to the mitral valve annulus is avoided, in order to let the chordae take the load without involving any rigid or nearly rigid reference like the annulus. Supra mitral device attachment to the mitral valve annulus may constrain the natural and effective load distribution on the multitude of untorn chordae.

As a further advantage, the supra mitral device stays attached/adherent to the posterior leaflet throughout the cardiac cycle; thus they move together. Consequently, there is no recurring encounter between the supra mitral device and the posterior leaflet in each heartbeat. This is as opposed to fixed plate-like devices, configured for attachment to the mitral valve annulus, where the posterior leaflets strike the plate in each systole, thus causing accumulated damage to the leaflet tissue.

According to some embodiments, the supra mitral device is made of a pliable material, adapted to stiffen slowly after implantation of the device. This advantageously enables the supra mitral device to adopt the anatomical shape of the leaflet tissue, maintaining the functioning chordae in their natural length, thereby preserving the even load distribution among them, while absorbing the systolic thrust of the LV pressure.

According to some embodiments, there is further provided an attachment/coupling element made of a memory shape material (e.g., smart metal alloy) or coiling tendency, configured to assume the function of a rivet and connect the supra mitral device to the desired part(s) of the mitral leaflets.

According to some embodiments, the attachment/coupling element(s) may have a size in the range of 3-15 mm, such as 5-7 mm or 4-10 mm.

According to some embodiments, the attachment/coupling element(s) may have a first spiral (the term "spiral" may also be referred to as a "coil") and a second spiral interconnected by an essentially straight wire. Each spiral may have a conus shape, the two conus shapes are facing each other at their bases, connected by the same wire that constitutes them, from the tip of the first conus to the tip of the second conus. According to some embodiments, the distal end of the first end forms the outermost loop of the first spiral, whereas the proximal end of the first end forms the innermost loop of the first spiral. Similarly, the distal end of the second end forms the innermost loop of the second spiral; whereas the proximal end of the second end forms the outermost loop of the second spiral. This configuration apposes the two wide bases of the conus shapes at each side of the two sheets it is meant to keep together; the mitral leaflet and supra mitral device material are held in position by the central wire tip to tip, and the elastic spring-like action of the spirals. This wide and elastic grip is meant to prevent tearing of the tissue to which it is attached when a pull force is applied at either end of the coupling element. For example, according to some embodiments, the coupling element is configured for attaching a supra mitral device to the mitral leaflets all around, in which case the spirals of the attachment/coupling element (rivets) are positioned on opposite sides of the supra mitral device and of the posterior leaflet, thereby causing attachment of the supra mitral device to the leaflet tissue. According to some embodiments, the basic wire structure may be with featherlike enveloping fibers. This is meant to cushion its touch on the tissue, as well as to form a skeleton for clots and tissue formation. The term "wire" does not imply it is necessarily metallic. It may be metallic, but may be of other materials, such as polymers, natural materials and other materials having inherent coiling characteristics (see for example, as exists in the plant Erodium Cicutarium ("stork's-bill")).

According to some embodiments, a second coupling element may be constructed by a couple of spirals connected to each other, for example, at their outer curve. This way it is only the wider outer curve of the spiral which is in touch with the leaflet and supra mitral device. The spirals' plane may be right angled to the supra mitral device/leaflet plane, and parallel to the chordae. The same principle may be expanded to two, three, or more couples of spirals in one coupling element.

According to some embodiments, a later second stage option exists, if residual mitral regurgitation is deemed unacceptable on follow-up, to employ the supra mitral device as a docking system for per-catheter mitral valve replacement.

According to some embodiments, there is provided herein a device for mitral valve repair in a subject in need thereof, the device comprising: a supra mitral device having essentially annular D-shape with an eccentric opening, such that a posterior section of the supra mitral device is wider than an anterior section of the supra mitral device, the posterior section of the supra mitral device configured for coverage and attachment to essentially the whole section of the posterior leaflet of the mitral valve which is facing the left atrium, thereby preventing and/or minimizing mitral regurgitation, wherein the posterior section of the supra mitral device is made of a pliable material, adapted to stiffen slowly after implantation of the device. According to some embodiments, the device is configured for trans-catheter implantation.

According to some embodiments, the posterior section of the supra mitral device is configured to stay attached/adherent to the part of the posterior leaflet, which is facing the left atrium, throughout the cardiac cycle, immobilizing the posterior leaflet to an essentially permanently elevated/closed position. The posterior section of the supra mitral device is attached to the posterior leaflet while assuming a shape of the posterior leaflet. Such shape may be wavy or curvy.

According to some embodiments, the supra mitral device is not directly attached to an annulus of the mitral valve. The supra mitral device may further comprise a plurality of through holes for securing the device to the mitral valve leaflet.

According to some embodiments, the device may further include a plurality of coupling elements configured to attach the supra mitral device to the leaflet of the mitral valve. According to some embodiments, the plurality of coupling elements comprise a memory shape material (e.g., smart metal alloy) configured to assume a shape of a coiled (spiral) coupling element. The coiled coupling element may include a first spiral and a second spiral interconnected by an essentially straight wire.

According to some embodiments, the coupling element is configured to be horizontal relative to the valve plane and is formed of a wire having a first end and a second end; the first end forming the first spiral and the second end forming the second spiral; wherein a distal end of the first end forms the outermost loop of the first spiral, and a proximal end of the first end forms the innermost loop of the first spiral; and wherein a distal end of the second end forms the innermost loop of the second spiral and a proximal end of the second end forms the outermost loop of the second spiral.

According to some embodiments, the coupling element is configured to be vertical relative to the valve plane and is formed of a wire having a first end and a second end; the first end forming the first spiral and the second end forming the second spiral; wherein a distal end of the first end forms the innermost loop of the first spiral, and a proximal end of the first end forms the outermost loop of the first spiral; and wherein a distal end of the second end forms the outermost loop of the second spiral and a proximal end of the second end forms the innermost loop of the second spiral.

According to some embodiments, the first and second spirals are positioned on opposite sides of the supra mitral device and mitral leaflet, when attached.

According to some embodiments, the pliable material comprises a woven material (such as woven fabric) made by any type of weaving or knitting. Yarns applied for such material may include cotton, viscose, rayon, wool, polyester, acrylic, acrylonitrile, silk or any other natural or synthetic material. According to some embodiments, the pliable material comprises a non-woven material (such as non-woven fabric). According to some embodiments, the pliable material comprises felt. The pliable material may include Teflon, Dacron (Teflon and Dacron are trademarks), PTFE (Gortex, trademark), or any combination thereof. The face of the pliable material in contact with the mitral leaflet may be pre-treated to facilitate tissue ingrowths from the mitral tissue.

According to some embodiments, the device is used for treating a subject suffering from mitral insufficiency. The mitral insufficiency may include fibroelastic deficiency, myxomatous mitral valve, functional mitral regurgitation, or combinations thereof.

According to some embodiments, there is provided herein a coupling element comprising a wire comprising a memory shape material configured to assume a shape of a spiraled coupling element; wherein the spiraled coupling element comprises a first spiral and a second spiral interconnected by an essentially straight wire; wherein a distal end of the first end forms the innermost loop of the first spiral, and a proximal end of the first end forms the outermost loop of the first spiral; and wherein a distal end of the second end forms the outermost loop of the second spiral and a proximal end of the second end forms the innermost loop of the second spiral. According to some embodiments, the terms attachment element and coupling element may be interchangeably used and may refer to any element configured to connect the supra mitral device to the valve. For example, according to some embodiments, the coupling element may be soft to the touch, or soft on its contact surfaces. According to some embodiments, the coupling element may be elastic in order to provide spring-like/shock-absorbing characteristics, with a strong yet elastic central core. The coupling element(s) may be configured to attach the supra-mitral supra mitral device to the leaflets of a mitral valve. The first and second spirals may be positioned on opposite sides of the supra mitral device and mitral leaflet, when attached. The coupling element(s) may include featherlike enveloping fibers configured to cushion its touch on the tissue, as well as to form a skeleton for clots and tissue formation. According to some embodiments, the coupling element is configured to be horizontal relative to the valve plane (e.g., conus shapes). According to some embodiments, the coupling element is configured to be vertical relative to the valve plane ((e.g., the spiral elements). According to some embodiments, the coupling element may include a horizontal section adapted for positioning above the supra mitral device plane and a vertical section adapted for positioning below the leaflet plane. The vertical section is designed not to interfere with the function of the untorn chordae.

Transcatheter Mitral Valve Repair (TMVRr) for Secondary MR-Functional Mitral Regurgitation (FMR):

According to some embodiments, there is thus provided herein, a device and method for mitral valve repair in a subject suffering from FMR. The device includes a supra mitral supra mitral device having essentially annular D-shape with an eccentric opening, such that a posterior section of the supra mitral device is wider than an anterior section of the supra mitral device, the posterior section of the supra mitral device configured for coverage and attachment to essentially the entire circumference of the mitral leaflet, while extending above the posterior leaflet, without being attached at all to its inner part, and further extend to (significantly) overlap at least a portion of the posterior inner margins of the anterior leaflet of the mitral valve, thereby preventing and/or reducing mitral regurgitation, wherein the section of the posterior section of the supra mitral device which is configured to overlap and cover partially the anterior leaflet is made of a pliable material, adapted to stiffen after implantation of the device. According to some embodiments, in an FMR version of the device, there is no need for the device to follow the movements of the posterior leaflet—it actually substitutes the posterior leaflet at the annular level serving as posterior mitral leaflet augmentation, while the overlapping skirt over the anterior leaflet performs a reverse coaptation between the anterior and posterior leaflets.

According to some embodiments, the part of the posterior section of the supra mitral device that is configured to overlap at least a portion of the anterior leaflet may be made of a less traumatic material (like PTFE/Gortex® or treated pericard) than the rest of the supra mitral device.

According to some embodiments, the device is configured to be coupled to the circumference of the mitral valve, and configured to be coupled to (for example, by at least two inner coupling elements) to P1 and to P3 posterior leaflet segments. These are the less-tethered areas of the valve leaflets. Further LV remodeling causes stronger tethering, which then effects P1 and P3 more and more, pulling the augmented posterior leaflet down with them, thus preserving its coaptation with the anterior leaflet at least for an extended time of continuing LV remodeling.

According to some embodiments, the device does not include annuloplasty. However, its immobilization of the whole mitral circumference prevents further annular dilatation.

According to some embodiments, there is further provided herein a deployment tool configured to hold the supra mitral device in its folded configuration within a catheter and when the deployment tool with the folded device emerges from the catheter above the mitral valve, the deployment tool is configured to unfold the supra mitral device and to adjust it to its final position on the mitral valve. The deployment tool will be removed or detached after the device is attached to the leaflets. According to some embodiments, the deployment tool may have a form of an umbrella having a plurality of arms (such as 3-5, 4-6 or 5-8). The umbrella may have at least two configurations: a close configuration for holding the folded device within the catheter and an open configuration for deploying the device and adjusting the deployed device in its desired location and position.

According to some embodiments, there is further provided herein an attachment tool for providing the coupling elements to attach the supra mitral devices to the valve leaflets. According to some embodiments, the attachment tool is configured to facilitate the coupling of the supra mitral device to the valve leaflets when the device is held by a deployment tool (such as the umbrella type deployment tool).

According to some embodiments, the attachment tool may also have an umbrella structure. The umbrella like attachment tools may be configured to attach the coupling elements from the umbrella ribs (arms).

According to some embodiments, the attachment tool may be a part of the deployment tool. For example, the deployment tool may have a main umbrella structure, and the attachment tool may have a secondary umbrella structure (for example, inserted through the central pole of the main umbrella).

According to some embodiments, the attachment tool may be a separate tool, formed and or functioning independently from the deployment tool.

According to some embodiments, any one of the attachment tools disclosed herein may be one by one loaded with coupling elements or loaded with a cartridge of coupling elements. The cartridge of coupling elements may include separate coupling elements or a line (such as a wire) from which the coupling elements are produced (e.g., cut) during the process of valve repair.

According to some embodiments, there is provided herein a supra mitral device for mitral/tricuspid valve repair in a subject in need thereof, the device comprising a main body portion having essentially annular D-shape with an eccentric opening, such that a posterior section of the main body portion is wider than an anterior section of the main body portion, the posterior section of the main body portion configured for coverage and attachment to essentially the whole section of the posterior leaflet of the mitral valve which faces the left atrium on systole, thereby preventing and/or reducing mitral regurgitation, wherein the posterior section of the main body portion is made of a pliable material, adapted to stiffen after implantation of the device. According to some embodiments, the subject may suffer from mitral insufficiency. The mitral insufficiency may include fibroelastic deficiency, myxomatous mitral valve, functional mitral regurgitation (FMR), or combinations thereof. According to some embodiments, the supra mitral device may be configured for trans-catheter implantation.

According to some embodiments, "essentially the whole section of the posterior leaflet of the mitral valve which faces the left atrium on systole" may refer to over 80% of the section of the posterior leaflet of the mitral valve which faces the left atrium on systole, over 90% of the section of the posterior leaflet of the mitral valve which faces the left atrium on systole, over 95% of the section of the posterior leaflet of the mitral valve which faces the left atrium on systole or between 80-95% of the over 90% of the section of the posterior leaflet of the mitral valve which faces the left atrium on systole.

According to some embodiments, the posterior section of the main body portion is configured to stay attached/adherent/bonded to the posterior leaflet throughout the cardiac cycle, eventually maintaining/immobilizing the posterior leaflet at an essentially permanently elevated/closed position.

According to some embodiments, the posterior section of the main body portion is attached to the posterior leaflet while assuming a shape of the posterior leaflet.

According to some embodiments, the main body portion is not directly attached to an annulus of the mitral valve.

According to some embodiments, the main body portion may further include a plurality of through holes for securing the device to the mitral valve leaflet.

According to some embodiments, the pliable material may include felt and/or, cloth, woven or knitted. The felt may include Teflon™, Dacron™, PTFE (Gortex™), or any combination thereof.

According to some embodiments, the main body portion has a stiffness gradient between an outer and an inner perimeter thereof.

According to some embodiments, the supra mitral device may further include an enforcement element extending along an inner perimeter of the main body portion.

According to some embodiments, the supra mitral device may further include an enforcement element extending along at least a part of an inner perimeter of the main body portion configured to support a particular location of the posterior leaflet where a leakage occurs.

According to some embodiments, the posterior section of the main body portion is configured to extend beyond the area of the posterior leaflet and thus to overlap a portion of an anterior mitral leaflet, thereby preventing/reducing mitral regurgitation.

According to some embodiments, the main body portion may further include an extension, contiguous with or attached to the posterior section and configured to extend beyond the area of the posterior leaflet and thus, when implanted, to overlap with a posterior part of an anterior leaflet, thereby preventing/reducing mitral regurgitation. The extension may be made of a less traumatic material than that of the posterior section.

According to some embodiments, there is provided herein a coupling element comprising a wire comprising a memory shape material configured to assume a spiral shape; wherein the spiral comprises a first spiral and a second spiral interconnected by an essentially straight wire; wherein a distal end of the first end forms the innermost loop of the first spiral, and a proximal end of the first end forms the outermost loop of the first spiral; and wherein a distal end of the second end forms the outermost loop of the second spiral and a proximal end of the second end forms the innermost loop of the second spiral.

According to some embodiments, there is provided herein a coupling element comprising a wire comprising a memory shape material configured to assume a spiral shape; wherein the spiral comprises a first spiral and a second spiral interconnected by an essentially straight wire; wherein a distal end of the first end forms the outermost loop of the first spiral, and a proximal end of the first end forms the innermost loop of the first spiral; and wherein a distal end of the second end forms the innermost loop of the second spiral and a proximal end of the second end forms the outermost loop of the second spiral.

According to some embodiments, there is provided herein the coupling element which may be configured to attach the supra-mitral main body portion disclosed herein or any other supra-mitral device to the leaflets of a mitral valve. The first and second spirals may be positioned on opposite sides of the main body portion and mitral leaflet, when attached.

According to some embodiments, the coupling element may include featherlike enveloping fibers configured to cushion its touch on the tissue, as well as to form a skeleton for clots and tissue formation.

According to some embodiments, there is provided herein a method of Per Cutaneous Mitral Valve Repair or Replacement (PCMVR), the method comprising attaching a supra mitral device disclosed herein or any other supra mitral device, supra mitrally, to a posterior leaflet along its outer and inner margins, thus coupling the device to the entire posterior mitral leaflet section that faces the left atrium on systole, and to the anterior leaflet at its outer margins only, thus completing attachment of the main body portion to the circumference of the mitral valve. Attaching may include using multiple coupling elements disclosed herein or other appropriate coupling elements.

According to some embodiments, the method may further include a later second stage step, if residual mitral regurgitation is deemed unacceptable on follow-up, to exploit the device as a docking system for per-catheter mitral valve replacement.

According to some embodiments, there is provided herein a method of Per Cutaneous Mitral Valve Repair or Replacement (PCMVR), the method includes supra mitrally attaching the device disclosed herein to a posterior leaflet along its outer and inner margins, thus coupling the device to the entire section of the posterior mitral leaflet, which faces the left atrium, and to the anterior leaflet at its outer margins only, thus completing attachment of the supra mitral device to all of the circumference of the mitral valve leaflets.

According to some embodiments, there is provided herein a method of Per Cutaneous Mitral Valve Repair or Replacement (PCMVR), the method includes supra mitrally attaching the device disclosed herein to all of the circumference only of the mitral valve leaflets, while the posterior leaflet along its inner margins as well, by either a second line of small coupling elements along its inner margins, or employing large coupling elements (for example, 8-15 mm diameter) along the posterior leaflet (mostly along its middle segment, the P2) this way, coupling the device to the entire section of the posterior mitral leaflet which faces the left atrium on systole, and to the anterior leaflet at its outer margins only (so this way the anterior leaflet retains its movement range near normal).

The method may further include a second, later step of employing the device as a docking system for per-catheter mitral valve replacement, if residual mitral regurgitation is deemed unacceptable on follow-up.

According to some embodiments, there is provided herein a method of Per Cutaneous Mitral Valve Repair or Replacement (PCMVR). The method includes supra mitrally attaching the device (supra mitral device) disclosed herein to the outer margin of the whole mitral valve circumference, while in the posterior leaflet along its outer and inner margins, thus coupling the device to essentially the entire section of the posterior mitral leaflet, which is facing the atrium. The method may further include employing the device as a docking system for per-catheter mitral valve replacement, wherein the supra mitral device is used as a docking system for mitral valve replacement are performed at the same single procedure. Attachments may include using multiple coupling elements/rivets as disclosed herein.

According to some embodiments, there is provided herein a method of Per Cutaneous Mitral Valve Repair or Replacement (PCMVR), for both primary (Degenerative) and secondary (Functional) mitral regurgitation. The method includes the steps of:

a. Inserting the deployment and attachment tools Transcatheter Percutaneously (separately or combined, according to the tools configuration): Trans-venous for trans-septal approach to the left atrium and mitral valve, Trans-arterial for retrograde approach through a large vessel to the aorta, aortic valve, left ventricle and mitral valve. Transapical approach may be employed in early models.

b. introducing the deployment tool into the left atrium just above the mitral valve. The deployment tool contains the device folded on it.

c. The deployment tool unfolds the device above the mitral valve circumference.

d. Aligning the device above the mitral valve: Both the mitral valve and the device are asymmetric: "D" shaped-like. The device is rotated to align the device above the mitral valve to its final alignment. The D shaped form of the device will be aligned to the D shape form of the mitral valve.

e. The device is positioned to cover the whole mitral valve, above its all circumference. The device asymmetric fenestration positioned to cover most of the anterior leaflet, except its base (close to the annulus, along the aortic-mitral continuity). The device is now ready to be attached.

f. The attachment tool (for, example, according to embodiments disclosed herein) ready to attach the device to the mitral valve leaflets. The attachment tool is loaded with coupling elements, single or multiple configuration.

g. The attachment tool is attaching the device to the mitral valve leaflets by inserting the coupling elements all around the mitral circumference on the leaflets themselves (near, but not on, the annulus). The trigger to the coupling tool for inserting a coupling element in order to attach the device to the mitral leaflet is synchronized to the ventricular systole. During the systole, the high left ventricular pressure keeps the leaflets up and tense to support the insertion by giving an opposite stabilizing force.

h. The insertion has three stages: First insert the coupling element to penetrate the device and mitral leaflet. The tip starts immediately to coil into a spiral below the mitral leaflet. Second the interventional cardiologist should decide whether the coupling element is well inserted and positioned: If not, the coupling element can still be retrieved by simply pulling by the coupling tool, then repeating the insertion process. If well inserted, the interventional cardiologist further releases the coupling element from the insertion tool. The upper/proximal part of the coupling element starts immediately to spiral above the device (in the left atrium). The two spirals are now attaching the device and leaflet. If the interventional cardiologist wishes then to retrieve the coupling elements, it might still be possible. When the interventional cardiologist approves this insertion step, the coupling element is detached from the attachment tool. The same procedure may be repeated with the next coupling elements as required. This technique may be used to insert a line or two lines of coupling elements along all of the mitral valve circumference (perimeter). According to some embodiments, the interventional cardiologist may have different sizes and types of coupling elements and may decide what sizes and types to use, as well as their number, and whether to put them in one line or two lines, to achieve complete immobilization of the posterior leaflet part facing the left atrium.

According to some embodiments, there is provided herein a kit for Per Cutaneous Mitral Valve Repair or Replacement (PCMVR), the kit comprising: a supra mitral device, disclosed herein in accordance with some embodiments; and a plurality of coupling elements, disclosed herein in accordance with some embodiments, configured to attach the main body portion to the leaflet of the mitral valve.

According to some embodiments, the plurality of coupling elements may include a memory shape material configured to assume a shape of a spiral. The coupling element may include a first spiral and a second spiral interconnected by an essentially straight wire.

According to some embodiments, the coupling element may be configured to be positioned horizontal relative to the valve plane and is formed of a wire having a first end and a second end; the first end forming the first spiral and the second end forming the second spiral; wherein a distal end of the first end forms the outermost loop of the first spiral, and a proximal end of the first end forms the innermost loop of the first spiral; and wherein a distal end of the second end forms the innermost loop of the second spiral and a proximal end of the second end forms the outermost loop of the second spiral.

According to some embodiments, the coupling element may be configured to be positioned vertical relative to the valve plane and is formed of a wire having a first end and a second end; the first end forming the first spiral and the second end forming the second spiral; wherein a distal end of the first end forms the innermost loop of the first spiral, and a proximal end of the first end forms the outermost loop of the first spiral; and wherein the distal end of the second end forms the outermost loop of the second spiral and a proximal end of the second end forms the innermost loop of the second spiral.

According to some embodiments, the first and second spirals may be positioned on opposite sides of the main body portion and mitral leaflet, when attached.

According to some embodiments, the kit may further include an artificial valve.

According to some embodiments, the kit may further include a deployment tool (for example, as disclosed herein in accordance with some embodiments) configured to deploy the supra mitral device and to adjust it to its final position on the mitral valve.

According to some embodiments, the kit may further include an attachment tool (for example, as disclosed herein in accordance with some embodiments) configured to provide the coupling elements.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 1D' schematically illustrates a top view of the supra mitral device illustrated in FIG. 1A, which also depicts the attachment/coupling element, according to some embodiments;

DETAILED DESCRIPTION

Figure 1:
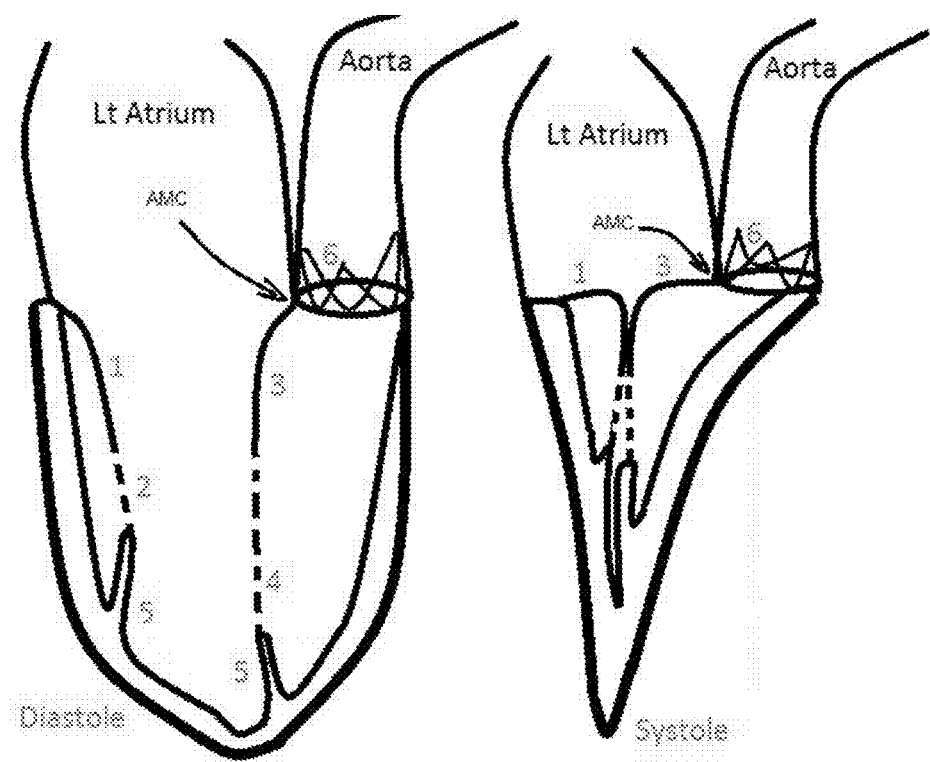
FIG. 1 schematically illustrates the mitral valve region.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a device for mitral valve repair in a subject in need thereof, the device comprising a supra mitral device having an essentially annular D-shape and an eccentric opening, such that a posterior section of the supra mitral device is wider than an anterior section of the supra mitral device.

According to some embodiments, as used herein, the term "supra mitral device" refers to a soft plate-like device configured for attachment to the leaflets of the mitral valve. Attachment of the supra mitral device to the posterior leaflet of the mitral valve prevents and/or minimizes mitral regurgitation. According to some embodiments, the posterior section of the supra mitral device is configured for attachment to a part of the posterior leaflet, which is facing the atrium. According to some embodiments, the anterior section of the supra mitral device is configured for attachment only to the part of the anterior leaflet of the mitral valve closest to the base of the anterior leaflet, at the aortic-mitral continuity level.

According to some embodiments, at least the posterior section of the supra mitral device is made of a pliable material, anticipated to stiffen slowly after implantation of the device. The pliability advantageously enables the supra mitral device to adopt the anatomical shape of the leaflet tissue, thereby preserving the relation of the leaflet to the untorn chords so that during every systole all the chords will be stretched to their pre-procedural length in which they functioned efficiently and take their fair part of the work load. The coupling of the supra mitral device to the leaflets means the supra mitral device moves with the leaflets, thus it hinders the leaflet from striking the supra mitral device during the dynamics of the cardiac cycle. Furthermore, the initial flexibility of the device enables it to assume a collapsed configuration suitable for delivery through a catheter. According to some embodiments, the pliable material comprises felt, typically made of Teflon™/Dacron™/PTFE (Gortex™), and the like, and/or woven of knitted cloth.

According to some embodiments, the supra mitral device is supra mitral, i.e. is configured to be attached to the mitral valve from the aspect of the leaflet facing the left atrium. According to some embodiments, the supra mitral device is configured to expand into its desired configuration upon its delivery into the left atrium.

According to some embodiments, the supra mitral device is configured to stay attached and bonded to the leaflets throughout the cardiac cycle and move with them, thereby hindering the leaflet from hitting the supra mitral device during systole. According to some embodiments, attachment of the supra mitral device to the posterior leaflet, eventually with time, maintains the leaflet in an essentially permanently elevated/closed position. It is thus understood that attachment of the supra mitral device causes the opening of the mitral valve to be constituted by anterior leaflet only. According to some embodiments, part of the mitral valve opening remains closed as a result of supra mitral device attachment to the posterior leaflet rim and free margin. According to some embodiments, 10%-50% of the mitral valve opening remains closed/ineffective as a result of supra mitral device attachment when the valve is in its open position (during diastole). This can be considered a kind of "one leaflet mitral valve repair", which is applied in many techniques of surgical mitral valve repairs.

According to some embodiments, the supra mitral device is configured to be attached to the valve tissue. According to some embodiments, the supra mitral device is not attached directly to a muscle tissue. According to some embodiments, the supra mitral device is not directly attached to the annulus of the mitral valve. This is highly advantageous in that attachment of the supra mitral device to the annulus may inevitably cause uneven tension distribution along the leaflets, thus, in turn, may cause tearing forces and ineffective supra mitral device coupling.

According to some embodiments, the terms attach/attached/attachment and couple/coupled/coupling may be used interchangeably.

According to some embodiments, the supra mitral device is formed of a material which enables penetration of coupling elements. According to some embodiments, the device includes a plurality of coupling elements configured to attach the supra mitral device to the posterior and anterior leaflets of the mitral valve. According to some embodiments, the coupling elements may be an integral part of the supra mitral device. Alternatively, the coupling elements may be stand-alone elements configured to penetrate the supra mitral device and bring about its attachment/coupling to the leaflets of the mitral valve. As used herein, the term "plurality" with regards to coupling elements may refer to at least 2, at least 3, at least 4, at least 10 or at least 15 coupling elements. Each possibility is a separate embodiment.

As used herein the term "coupling element" may refer to any element configured to accomplish the attachment/coupling/bonding/securing/affixing of the supra mitral device to the leaflets of the mitral valve. According to some embodiments, the coupling element may include staples, straps, hooks, screws, pins, bolts, rivets, or any other suitable coupling element or combination of coupling elements. According to some embodiments, the coupling element includes a memory shape material configured to assume the shape of a coiled coupling element or spiral coupling element, as further elaborated hereinbelow. According to some embodiments, the term "coupling element" refers to a mechanical fastener including a shaft (e.g. a straight wire or cylinder) with fastening elements at each end. According to some embodiments, the coupling element may initially have a form of a straight wire configured to penetrate the supra mitral device and the leaflet. After penetration, the wire folds into a predetermined dumbbell-like configuration which holds the coupling element in place. According to some embodiments, the predetermined shape of the coupling element may be in the form of two horizontal (parallel to the leaflets) spirals or vertical (perpendicular to the leaflets) spirals connected by a straight wire. According to some embodiments, the wires twist into spirals which are positioned on opposite sides of the supra mitral device and of the posterior leaflet, when attached. According to some embodiments, the wires twist into spirals which are vertically positioned relative to the straight wire (the spirals). According to some embodiments, the spirals may be horizontally positioned (the conuses) right angled to the connecting straight wire. According to some embodiments, one of the spirals may be horizontally positioned and the other vertically positioned relative to the straight wire. According to some embodiments, the predetermined shape of the coupling element may include two double spirals separated by a straight wire.

According to some embodiments, the wire forming the coupling element has a first end and a second end, wherein the first end forms the first spiral and the second end forms the second spiral. According to some embodiments, the distal end of the first end forms the outermost loop of the first spiral, whereas the proximal end of the first end forms the innermost loop of the first spiral. Similarly, the distal end of the second end forms the innermost loop of the second spiral, whereas the proximal end of the second end forms the outermost loop of the second spiral. This advantageously prevents tearing of the tissue to which it is attached when a pull force is applied at either end of the coupling element, as it has a spring like spiral configuration which absorbs the pulling force.

According to some embodiments, the coupling element is configured to be vertical relative to the valve plane and is formed of a wire having a first end and a second end; the first end forming the first spiral and the second end forming the second spiral; wherein a distal end of the first end forms the innermost loop of the first spiral, and a proximal end of the first end forms the outermost loop of the first spiral; and wherein a distal end of the second end forms the outermost loop of the second spiral and a proximal end of the second end forms the innermost loop of the second spiral.

According to some embodiments, the device is suitable for use in a subject suffering from mitral insufficiency resulting from fibro-elastic deficiency, myxomatous mitral valve, functional mitral regurgitation, or combinations thereof. Each possibility is a separate embodiment.

According to some embodiments, the coupling element is configured to attach a supra mitral device to a posterior leaflet of a mitral valve and the anterior leaflet, as essentially described herein.

According to some embodiments, the first and second spirals are positioned on opposite sides of the supra mitral device, when attached, as essentially described herein.

Reference is now made to FIG. 1, which schematically depicts the mitral valve region and operation (during systole and diastole). The following numbers depict the respective parts in the valve region:
1—Posterior mitral leaflet;
2—Chordae;
3—Anterior mitral leaflet;
4—Chordae;
5—Papillary muscles; and
6—Aortic valve Reference is now made to FIG. 1A-F, which schematically illustrate top and perspective views respectively, of a supra mitral device 100 for trans-catheter mitral valve repair, according to some embodiments. Supra mitral device 100 has an essentially annular, D shape and an eccentric opening 110, the opening located such that a posterior (marked as "P") section 120 of supra mitral device 100 is wider than an anterior (marked as "A") section 122 of supra mitral device 100.

Figure 1A:
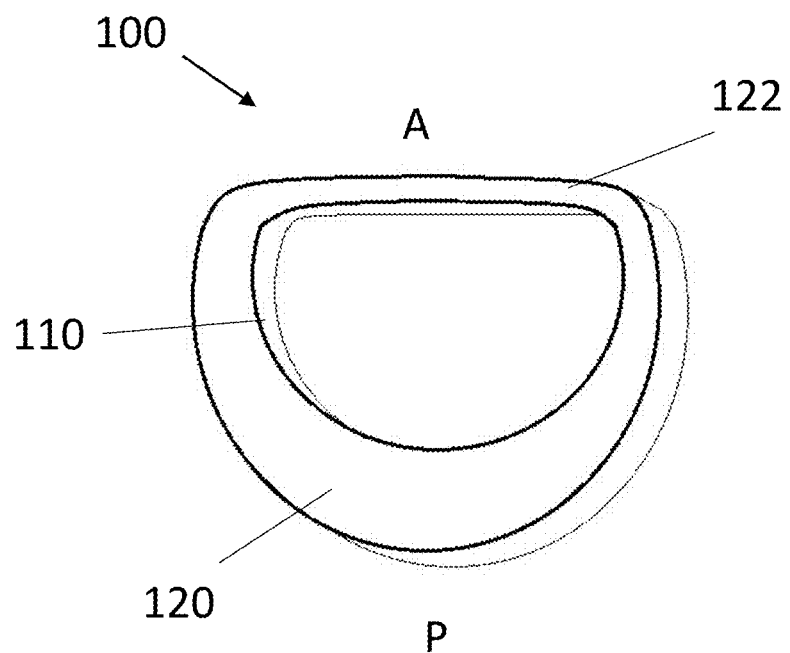
FIG. 1A schematically illustrates a top view of a supra mitral device for trans-catheter mitral valve repair, according to some embodiments.
Figure 1B:
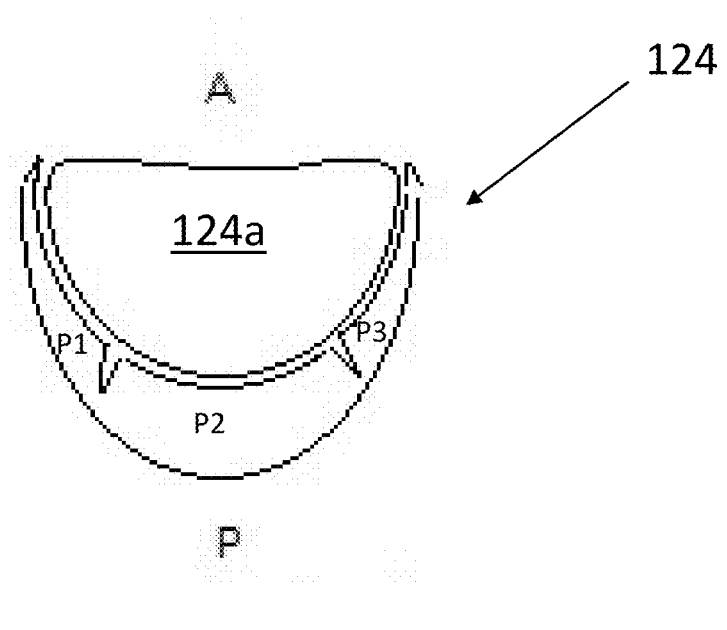
FIG. 1B schematically illustrates a top view of the valve leaflets without the supra mitral device, according to some embodiments.
Figure 1C:
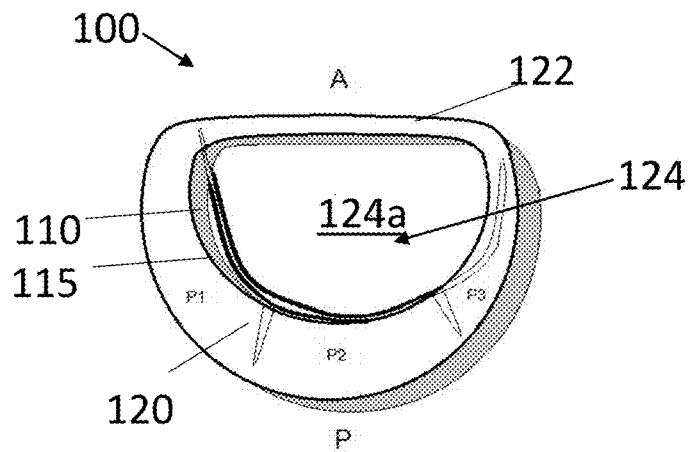
FIG. 1C schematically illustrates a top view of the supra mitral device illustrated in FIG. 1A, also depicting the valve leaflets seen below the supra mitral device, according to some embodiments.

FIG. 1B schematically illustrates a top view of a valve 124 without a supra mitral device, according to some embodiments. Valve 124 has an anterior leaflet 124a and a posterior leaflet which has three sections depicted as P1, P2 and P3. FIG. 1C schematically illustrates a top view of the supra mitral device illustrated in FIG. 1A and also depicting the leaflets of valve 124 seen below the supra mitral device, according to some embodiments. Supra mitral device 100 is configured for attachment to the leaflets of the mitral valve at the aspect facing the atrium such that opening 110 at least partially lines the opening of the anterior leaflet of the mitral valve as shown in FIG. 1C.

Attachment of supra mitral device 100 to the posterior leaflet of the mitral valve prevents and/or mitigates flailing of mitral segments, thus minimizing mitral regurgitation. Posterior section 120 of supra mitral device 100 is configured for attachment to the posterior leaflet of the mitral valve, and anterior section 122 of supra mitral device 100 is configured for attachment to the part of the anterior leaflet of the mitral valve closest to the base of the anterior leaflet, at the aortic-mitral continuity (AMC) region as seen in FIG. 1.

At least posterior section 120 of supra mitral device 100 (optionally the entire supra mitral device 100) is made of a pliable material, adapted to slowly stiffen after implantation thereof. This advantageously enables supra mitral device 100 to adopt the anatomical shape of the leaflet tissue, thereby preventing the leaflet from striking against supra mitral device 100 during the dynamics of the cardiac cycle. Similarly, supra mitral device 100 is configured to stay attached/adhered/bonded to the posterior leaflet throughout the cardiac cycle, thereby preserving the relation of the leaflet to the non-torn chords' length, such that during every systole all the non-torn chords will be stretched to their proper length and take their fair share of the work load. The coupling of the supra mitral device to the leaflets means that the supra mitral device moves with the leaflets, thus it hinders the leaflets from striking against the supra mitral device during the dynamics of the cardiac cycle during the systole.

Opening 110 is defined by an inner perimeter 115 of supra mitral device 100. According to some embodiments, inner perimeter 115 may be configured to provide support to the leaflets of valve 124. According to alternative or additional embodiments, inner perimeter 115 may be configured to provide docking to an artificial valve.

According to some embodiments, supra mitral device 100 is configured to be attached supra mitrally, i.e. on the aspect of the leaflet facing the left atrium.

According to some embodiments, supra mitral device 100 has a collapsed configuration (not shown) enabling its delivery through a catheter.

Figure 1D:
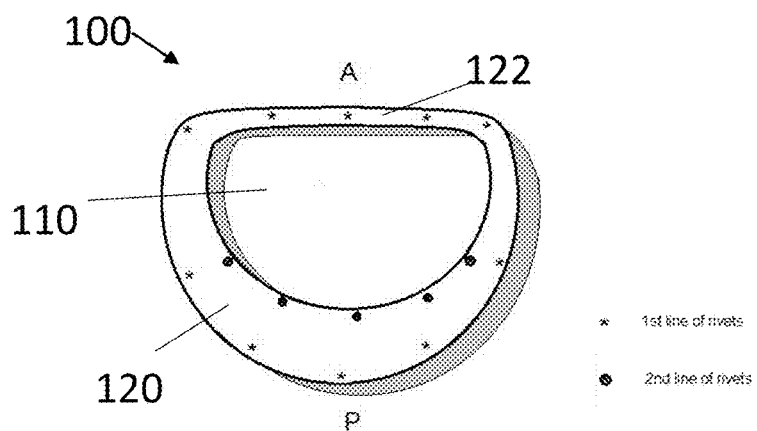
FIG. 1D schematically illustrates a top view of the supra mitral device illustrated in FIG. 1A, also depicting the attachment/coupling element, according to some embodiments.
Figure 1D:
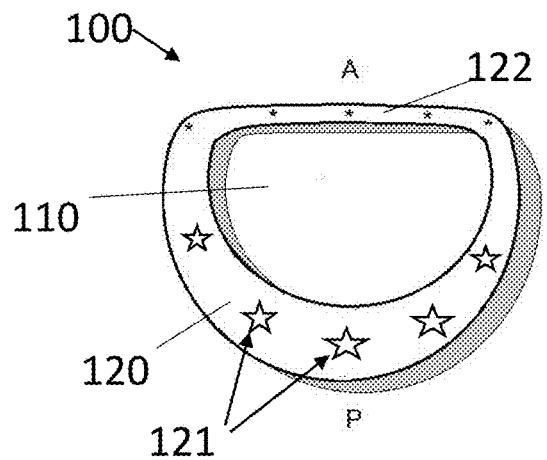

FIG. 1D schematically illustrates a top view of the supra mitral device illustrated in FIG. 1A, which also depicts the attachment/coupling element, according to some embodiments. The stars (***) represent the location of the coupling elements connecting the outer circumference of the supra mitral device to the leaflets of the mitral valve all around. The small circles (ooo) represent the location of the coupling elements connecting the inner margin of the posterior section of the supra mitral device to the inner margins of the posterior leaflet of the mitral valve.

FIG. 1D' schematically illustrates a top view of the supra mitral device illustrated in FIG. 1A, which also depicts the attachment/coupling element, according to some embodiments. The small stars (*) represent the location of the coupling elements connecting the outer circumference of the supra mitral device to the leaflets of the mitral valve at the anterior section of the supra mitral device. The large stars (121) represent the location of larger coupling elements (relative to the smaller coupling elements represented by the small stars (*)) connecting the posterior section of the supra mitral device to the posterior leaflet of the mitral valve. Employing large coupling elements on the posterior mitral leaflet, enables one line of coupling elements (as opposed to FIG. 1D) and optionally fewer coupling elements.

Figure 1E:
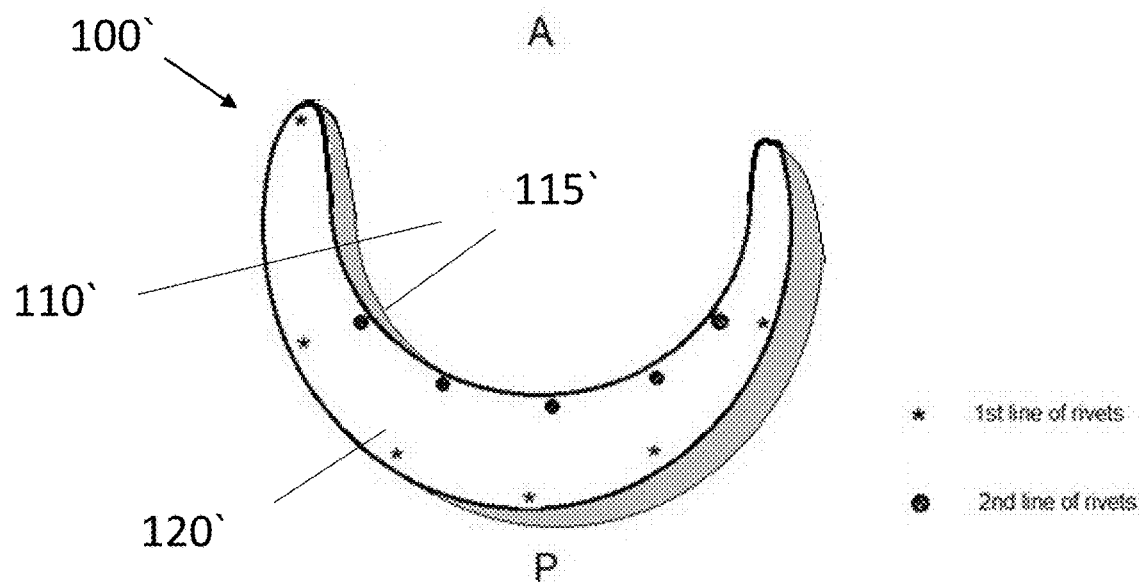
FIG. 1E schematically illustrates a top view of the "horse shoe" shaped supra mitral device and depicting the attachment/coupling element, according to some embodiments.
Figure 1F:
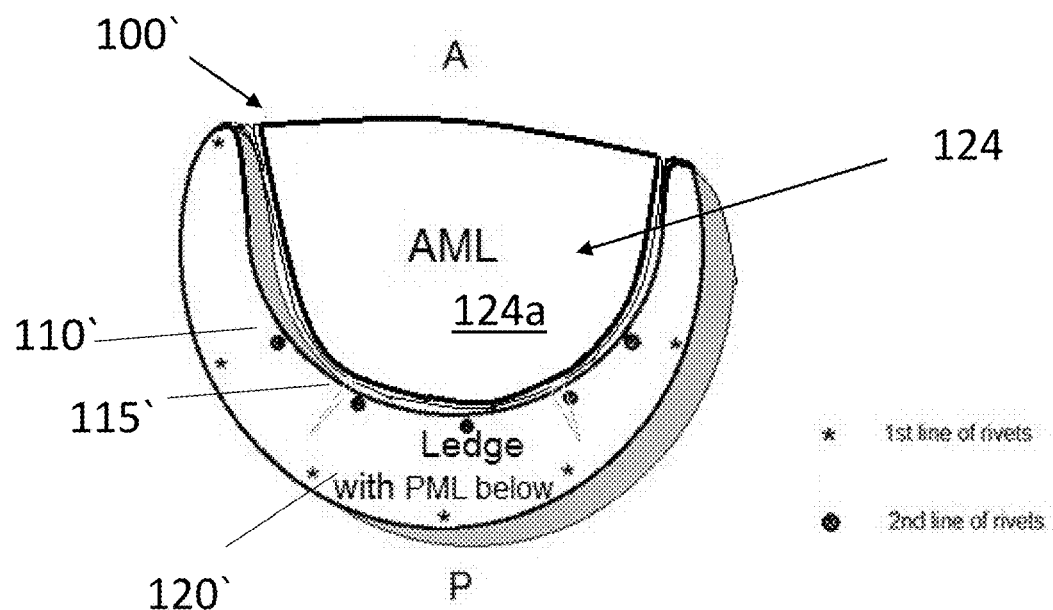
FIG. 1F schematically illustrates a top view of the supra mitral device of FIG. 1E, and also depicting the valve leaflets seen below the supra mitral device, according to some embodiments.

Reference is now made to FIG. 1E, which schematically illustrates a top view of the "horse shoe" shaped supra mitral device and depicting the attachment/coupling element, according to some embodiments and to FIG. 1F, which schematically illustrates a top view of the supra mitral device of FIG. 1E, and also depicting the valve leaflets seen below the supra mitral device, according to some embodiments.

Supra mitral device 100' has essentially a "horse shoe" shape 110', having only a posterior (marked as "P") section 120' where an anterior (marked as "A") section is missing. Supra mitral device 100' has an inner perimeter 115'. According to some embodiments, inner perimeter 115' may be configured to provide support to the posterior leaflet of valve 124. According to alternative or additional embodiments, inner perimeter 115' may be configured to provide docking to an artificial valve.

It is understood that embodiments of this disclosure include a supra mitral device such as supra mitral device 100, where the anterior section is partial or incomplete, such that the supra mitral device has a form of an unclosed ring (opened perimeter where the two ends of the supra mitral device are not joined), or any other shape which is configured for attachment to the posterior leaflet of the mitral valve.

Figure 1G:
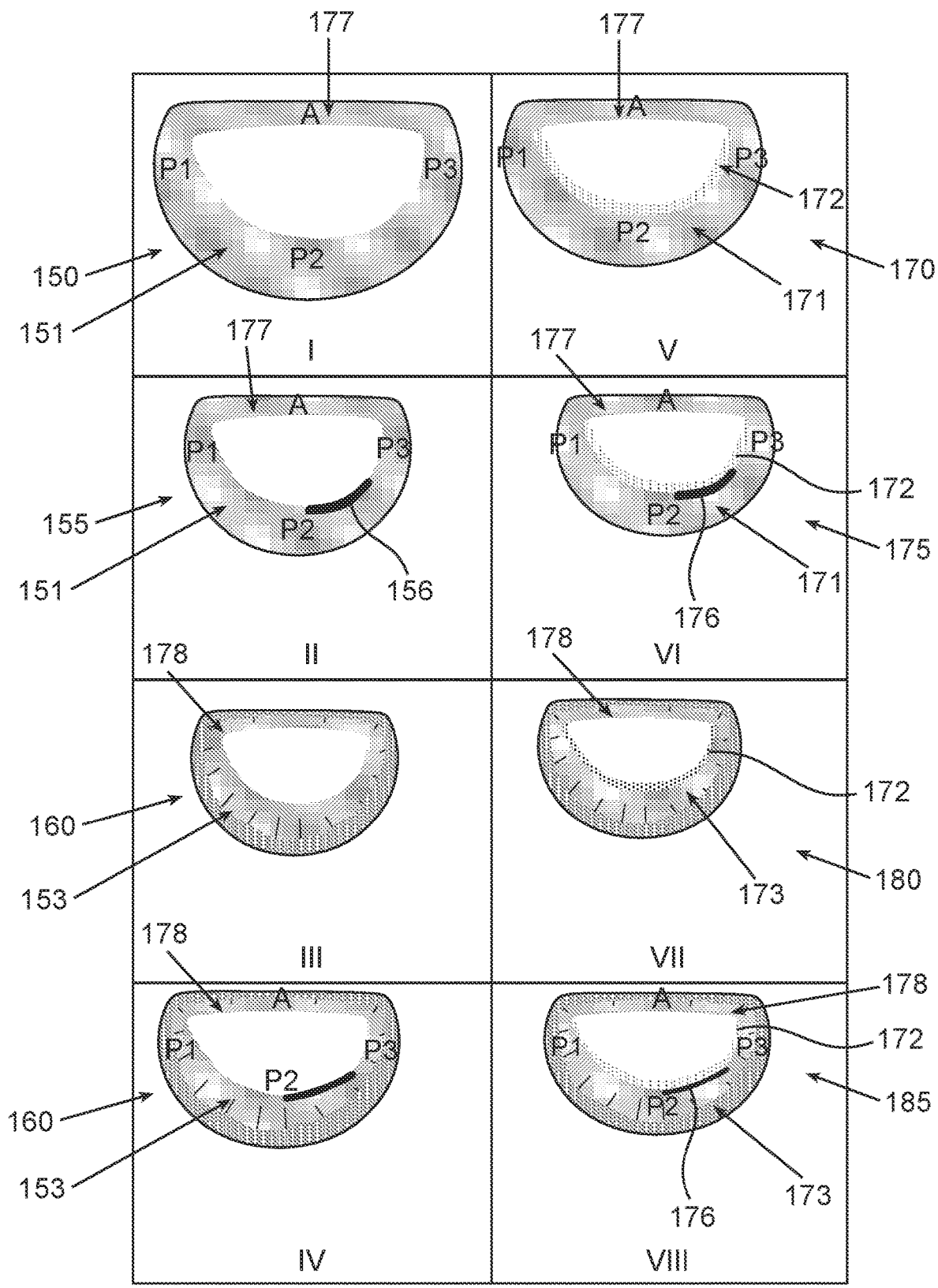
FIG. 1G I-VIII schematically illustrate different variations of supra mitral devices, according to some embodiments.

Reference is now made to FIG. 1G I-VIII, which schematically illustrate different variations of supra mitral devices, namely devices 150, 155, 160, 165, 170, 175, 180 and 185 respectively, according to some embodiments. Devices 150, 155, 160 and 165 (FIG. 1G I-IV) are configured for posterior mitral leaflet (P) immobilization without overlapping the anterior leaflet (A). According to some embodiments, devices 150, 155, 160 and 165, have a shape similar to that of device 100 (of FIG. 1A-D) and are configured for attachment to the posterior leaflet (P) of the mitral valve. Devices 150, 155, 160 and 165 have an anterior section 177/178 configured for attachment to a narrow strip at the base of the anterior leaflet of the mitral valve. Anterior section 177 has a unified softness, while anterior section 178 has a gradual softness, for example becoming softer from the external "ring" part to the internal "ring" part. Devices 150, 155, 160 and 165 have a posterior section 151/153 configured for attachment to the posterior leaflet (P) of the mitral valve. According to some embodiments, posterior section 151 has a unified softness, while posterior section 153 has a gradual softness, for example becoming softer from the external "ring" part to the internal "ring" part. According to some embodiments, devices 155 and 165, further have a local enforcement element 156 to support the particular location of the posterior leaflet where the leakage occurs.

Devices 170, 175, 180 and 185 (FIG. 1G V-VIII) are configured for posterior mitral leaflet (P) immobilization with some extra width to overlap a narrow strip at the inner margin of the anterior mitral leaflet.

According to some embodiments, devices 170, 175, 180 and 185, have a shape similar to that of device 100 (of FIG. 1A-D) and are configured for attachment to the posterior leaflet (P) of the mitral valve. Like devices 150, 155, 160 and 165, devices 170, 175, 180 and 185, have an anterior section 177/178 configured for attachment to a narrow strip at the base of the anterior leaflet of the mitral valve. However, unlike devices 150, 155, 160 and 165, devices 170, 175, 180 and 185 have a posterior section 171/173 configured for attachment to the posterior leaflet (P) of the mitral valve with some extra width (172) along an inner part thereof, to overlap a narrow strip at the inner margin of the anterior mitral leaflet. According to some embodiments, posterior section 171 has a unified softness, while posterior section 173 has a gradual softness, for example, becoming softer from the external "ring" part to the internal "ring" part. Like devices 150, 155, 160 and 165, devices 170, 175, 180 and 185 may further have a local enforcement element 176 to support the particular location of the posterior leaflet where the leakage occurs.

According to some embodiments devices 150, 155, 160, 165, 170, 175, 180 and 185 have two modes: open mode and close mode. When the devices are inside the catheter they are in a close mode, for example, attached to an umbrella device folded to their close mode. When the deployment tool, such as the umbrella with the folded device, emerges from the catheter above the mitral valve, the deployment tool, such as the umbrella, opens and the supra mitral device unfolds. The deployment tool, such as the umbrella, is configured to hold and adjust the device in its final position on the mitral valve. The deployment tool, such as the umbrella, will be removed or detached after attaching the device to the leaflets. Devices 150, 155, 160, 165, 170, 175, 180 may be made of one or more layers. Devices 150, 155, 160, 165, 170, 175, 180 may be made of one or more knitted Dacron like materials and/or other least traumatic materials (Pericard, Gortex, Gortex like or any other appropriate material).

Figure 2:
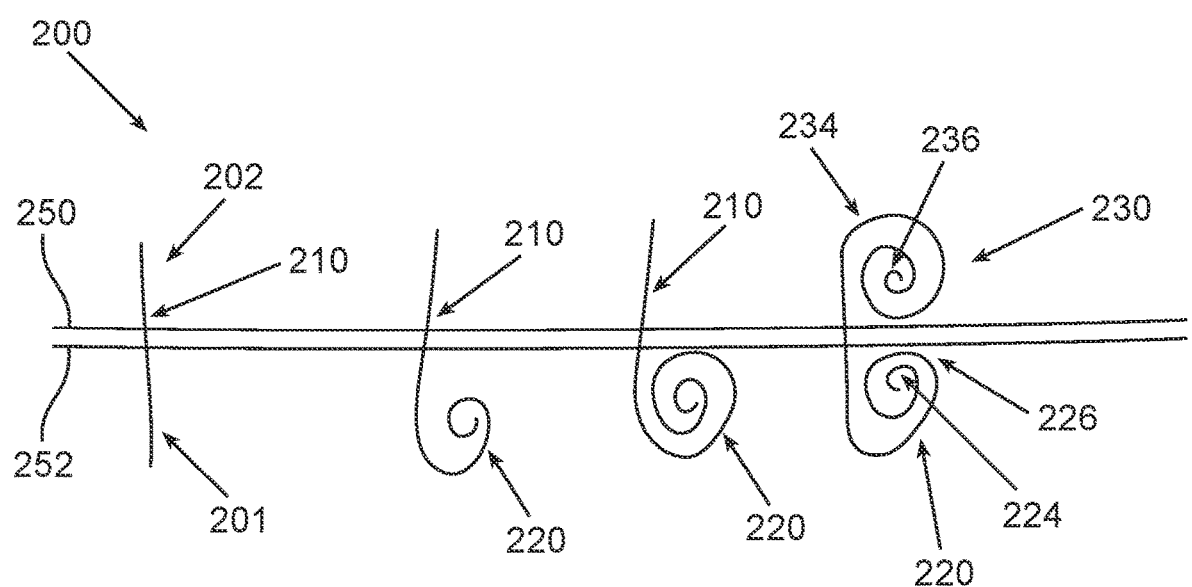
FIG. 2 schematically illustrates a vertical coupling element during its transformation from a straight wire to a double spiraled vertical coupling element; according to some embodiments.

Reference is now made to FIG. 2, which schematically illustrates a vertical coupling element 200 during its folding from a straight wire (step 1) to a double coiled vertical spiral coupling element (step 4); according to some embodiments. During delivery, coupling element 200 is a straight wire 210 (step 1). Subsequently, a first end 201 of wire 210 spirals into a first vertical spiral 220 (steps 2 and 3). In its straight or first end coiled configuration, coupling element 200 may penetrate the surfaces to be attached, such as, but not limited to, the supra mitral device and the posterior leaflet of the mitral valve, here illustrated as surfaces 250 and 252. After penetration, the second end 202 of wire 210 folds into a second vertical spiral 230 (step 4) such that first vertical spiral 220 and second vertical spiral 230 are positioned on opposite sides of surfaces 250 and 252 (step 4). First and second vertical spirals 220 and 230 are folded such that a distal end of first end 201 forms the innermost loop 224 of first vertical spiral 220, and a proximal end of first end 201 forms the outermost loop 226 of first vertical spiral 220. Similarly, a distal end of second end 202 forms the outermost loop 234 of second vertical spiral 230 and a proximal end of second end 202 forms the innermost loop 236 of second vertical spiral 230. This advantageously provides shock-absorbing quality of the coils to lessen direct forces exerting tearing effects on the delicate surfaces (e.g. tissue) to which it is attached when a pull force is applied at either end of the coupling element. Optionally, the diameter of wire 210 may be gradually decreasing toward ends 201 and 202 thereof, thereby easing the folding into spirals 220 and 230.

Figure 3A:
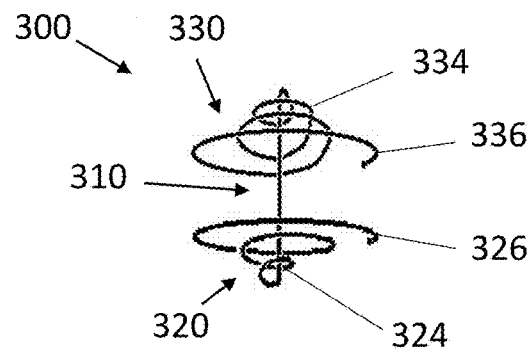
FIGS. 3A-C schematically illustrate horizontal coupling elements, according to some embodiments.
Figure 3B:
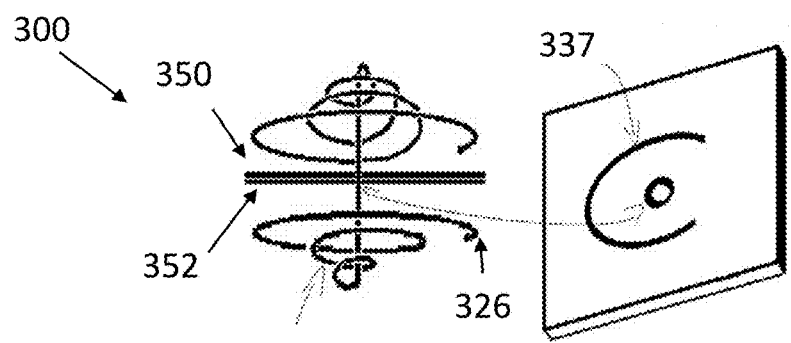
Figure 3C:
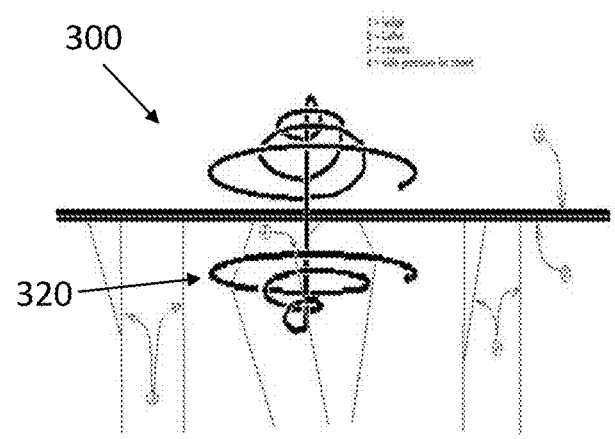

Reference is now made to FIGS. 3A-C, which schematically illustrate a horizontal coupling element, according to some embodiments. During delivery, coupling element 300 is a wire 310, which folds into a first horizontal spiral 320 and subsequently, after penetrating the surfaces to be attached, such as, but not limited to, the supra mitral device and the posterior leaflet of the mitral valve, here illustrated as surfaces 350 and 352 (FIG. 3B), into a second horizontal spiral 330 such that first horizontal spiral 320 and second horizontal spiral 330 are positioned on opposite sides of surfaces 350 and 352. First and second horizontal spirals 320 and 330 are folded such that a distal end of the part of the wire forming first spiral 320 forms the outermost loop 326 and a proximal end the part of the wire forming first spiral 320 forms the innermost loop 324 of first vertical spiral 220. Similarly, a distal end of the part of the wire forming second spiral 330 forms the innermost loop 334 and a proximal end of the part of the wire forming second spiral 330 forms the outermost loop 336. This advantageously prevents tearing of the delicate surfaces (e.g. tissue) to which it is attached when a pull force is applied at either end of the coupling element. Optionally, the diameter of wire 310 may be gradually decreasing toward its ends, thereby easing the folding into spirals 320 and 330. FIG. 3B shows the contact area 337 of outermost loop 326 of first vertical spiral 320 of horizontal coupling element 300 with the valve leaflet 352.

FIG. 3C further shows cords 3 and the side pressure on the chord 4 applied by first horizontal coupling element 320 of horizontal coupling element 300. This may limit the employment of horizontal coupling elements below the leaflet (on the ventricular aspect of the leaflets), where the chordae are attached.

Reference is now made to FIGS. 4A-E, which schematically show a two-sided single spiral vertical coupling element 200 (similar to the coupling element shown in FIG. 2), a two-sided double spirals vertical coupling element 400, a two-sided triple spirals vertical coupling element 400', and a two-sided quadruple spirals vertical coupling element 400', according to some embodiments. During delivery, coupling element 400 is a double stranded wire 410, which folds into a first double spirals vertical coupling element 420 and subsequently, after penetrating the surfaces to be attached, such as, but not limited to, the supra mitral device and the posterior leaflet of the mitral valve, here illustrated as surfaces 450 and 452, into a second double spirals vertical coupling element 430, such that first double spirals vertical coupling element 420 and second double spirals vertical coupling element 430 are positioned on opposite sides of surfaces 450 and 452, as essentially described herein. According to some embodiments, spirals vertical coupling elements can be doubled, tripled, quadrupled (or more), as the technology enables. This will increase the contact area of the spirals with the leaflet.

Figure 4A:
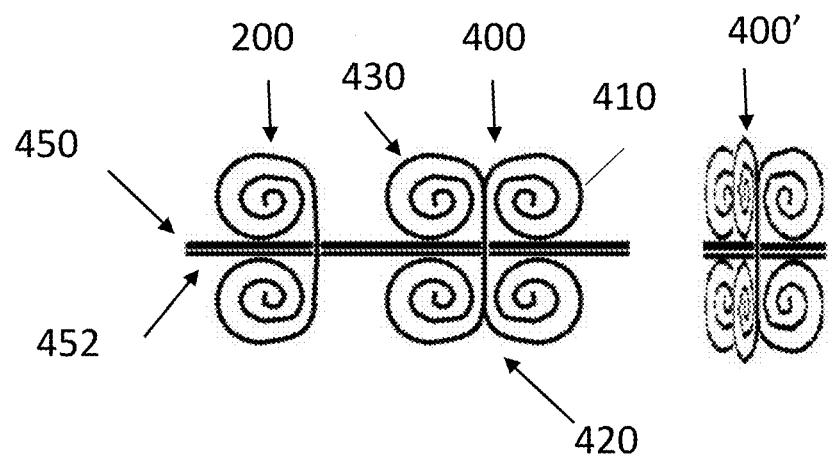
FIGS. 4A-E schematically illustrate single, triple and quadruple double spiraled vertical coupling elements, according to some embodiments.
Figure 4B:
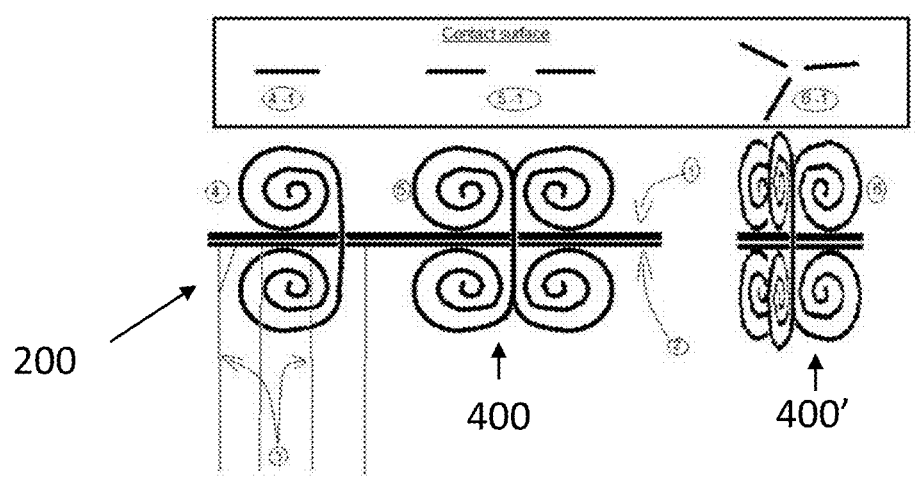

FIG. 4B, top, demonstrates, according to some embodiments, the respective contact surfaces of vertical coupling elements 200, 400 and 400' with the leaflet.

As further demonstrated in FIG. 4B, according to some embodiments, vertical coupling elements may be advantageous over horizontal coupling elements on the ventricular aspect of the mitral leaflets, as they do not apply side pressure on the chordae (FIG. 3C).

Figure 4C:
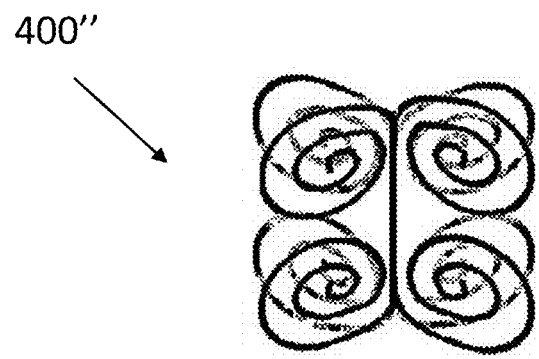
Figure 4D:
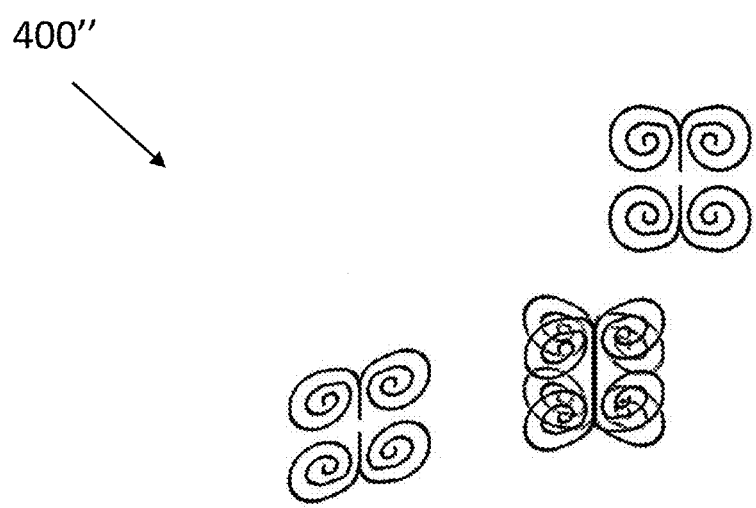
Figure 4E:
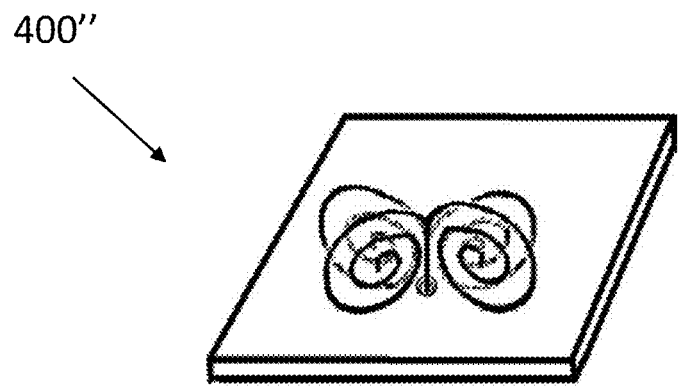

FIGS. 4C-E, demonstrate, according to some embodiments, a respective view (FIG. 4C), an assembled and partially assembled view (FIG. 4D) and a top isometric view (FIG. 4E) of a two-sided quadruple coiled vertical coupling element 400".

Figure 5:
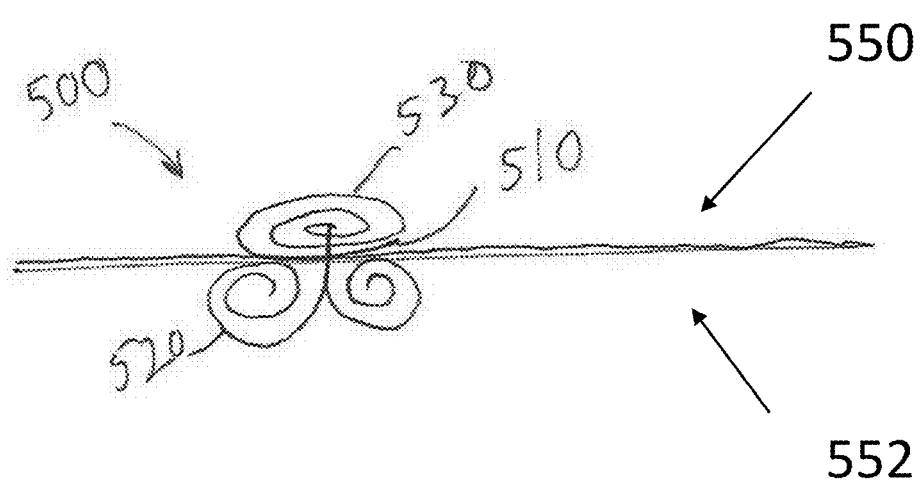
FIG. 5 schematically illustrates a combined coupling element including a two-sided lower vertical spiral and an upper horizontal spiral, according to some embodiments.

Reference is now made to FIG. 5, which schematically shows a combined coupling element 500, including a first double vertical spiral 520 and a second horizontal spiral 530; according to some embodiments. During delivery, coupling element 500 is a double stranded wire 510, which folds into first a double vertical spiral coupling element 520 and subsequently, after penetrating the surfaces to be attached, such as, but not limited to, the supra mitral device and the posterior leaflet of the mitral valve, here illustrated as surfaces 550 and 552, into second horizontal spiral coupling element 530, such that first double vertical spiral coupling element 520 and second horizontal spiral coupling element 530 are positioned on opposite sides of surfaces 550 and 552, as essentially described herein. The vertical spiral coupling element is positioned on the ventricular aspect of the leaflet; the horizontal coupling element is positioned on the atrial aspect of the supra mitral device.

Figure 6:
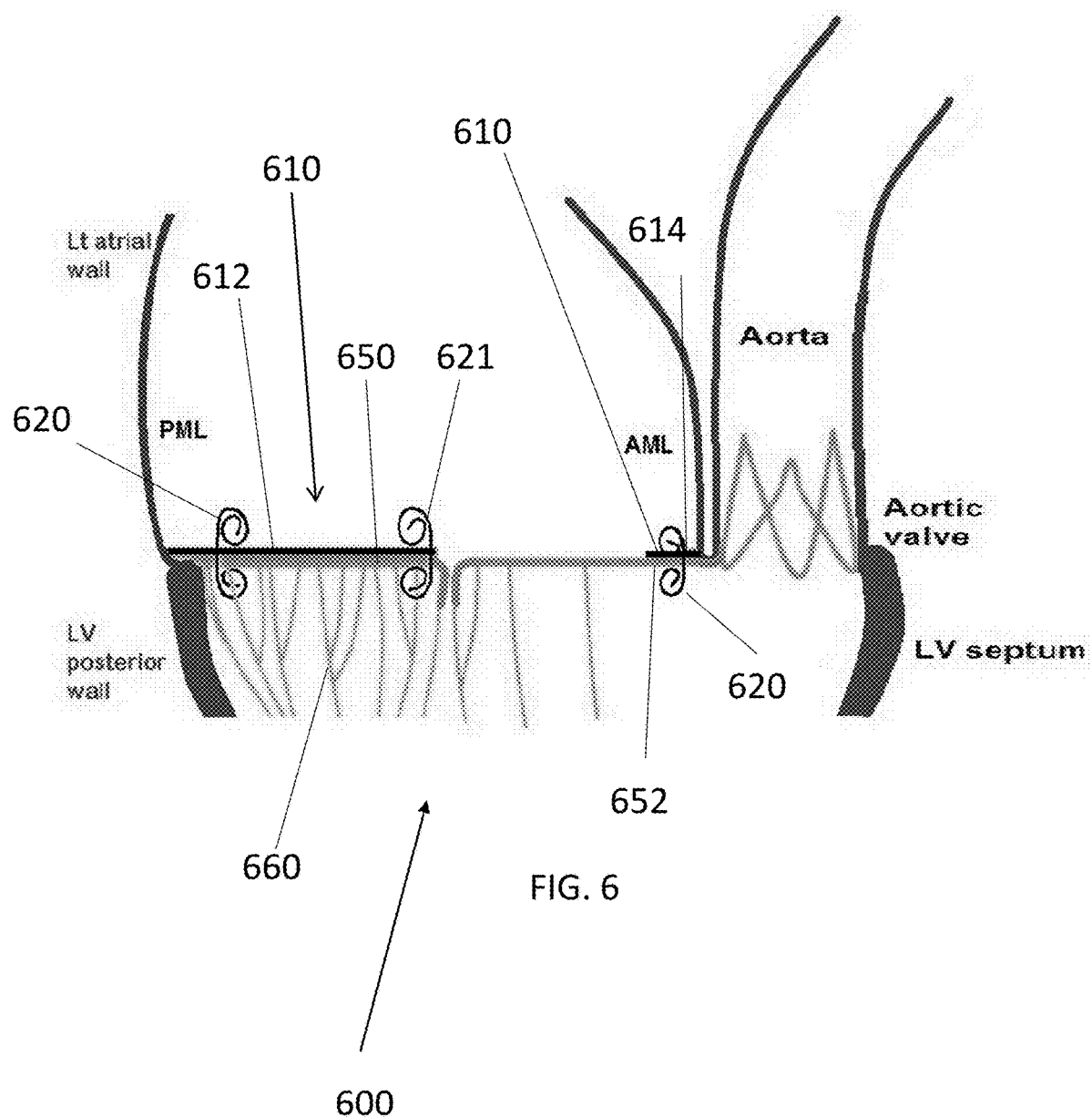
FIG. 6 schematically illustrates a supra mitral device for trans catheter mitral valve repair attached to the leaflets of a mitral valve using a plurality of coupling elements, according to some embodiments.

Reference is now made to FIG. 6, which schematically illustrates a mitral valve 600 having a supra mitral device 610 attached to its posterior leaflet 650 by a plurality of coupling elements 620/221; according to some embodiments. Supra mitral device 610 may be similar to supra mitral device 100 of FIG. 1A and FIG. 1B having an essentially annular D-shape and an eccentric opening located such that a posterior section 612 is attached to the posterior leaflet 650 of the mitral valve along its outermost and innermost margins (two lines of coupling elements: outer line of coupling elements 620 and inner line of coupling elements 621), and anterior section 614 of supra mitral device 600 is attached to the anterior leaflet 652, along its outermost margin only (one line of coupling elements), the aortic-mitral continuity area (shown and marked in FIG. 1), thereby preventing or reduce grade of mitral regurgitation.

The exact position of supra mitral device 610 ensures that posterior leaflet 650 is in its normal position during systole. At this position, the untorn chordae 660 of posterior leaflet 650 take all the load of the left ventricular systolic pressure (above 100 mmHg), which is just what they are used to doing. The supra mitral device, above the leaflet and bonded to it, is not taking any load at all by itself. At diastole, there is very little downward driving pressure, left arterial pressure only, pushing posterior section 612 of supra mitral device 600 toward the left ventricle. That is, supra mitral device 610 is positioned in a plane ensuring minimal forces thereon and consequently assuring successful adherence of supra mitral device 610 to posterior leaflet 650 with the coupling elements, after implantation. Thus, a low-load plane is identified and utilized just above the mitral leaflet, which facilitates good coupling and will allow good results in the treatment of regurgitant mitral valve.

According to some embodiments, a part of or the whole supra mitral device 610 is made of a pliable material, adapted to stiffen later after implantation has occurred. This advantageously enables supra mitral device 610 to adopt the anatomical shape of posterior leaflet 650, thereby preventing posterior leaflet 650 from striking against supra mitral device 610 during the dynamics of the cardiac cycle.

According to some embodiments, supra mitral device 610 is configured to attach supra mitrally, i.e. on the aspect of the leaflet facing the left atrium. According to some embodiments, supra mitral device 610 is configured to be attached to posterior leaflet 650 from within the left atrium, along its outer and inner margins, thus being coupled to (essentially) the entire posterior mitral leaflet section which faces the left atrium during systole. According to some embodiments, supra mitral device 610 is delivered through a delivery device.

Embodiments for exemplary delivery devices are presented herein but should not be considered limiting.

According to some embodiments, there is further provided herein a device for positioning the supra mitral device and/or deploying the coupling elements, to secure the supra mitral device in place.

Reference is now made to FIGS. 7A-L, which schematically illustrate various embodiments of deployment tools for deploying and positioning supra mitral devices on the valve. The deployment tools shown in FIGS. 7A-L are "umbrella" type tools. FIGS. 7B-L further illustrate attachment tools for providing the coupling elements to attach the supra mitral devices to the valve leaflets. The attachment tools may be "umbrella" type tools or non-umbrella type tools. The attachment tools may be a part of the "umbrella" type deployment tool or may be a non-umbrella separate tool.

According to some embodiments, the "umbrella" type deployment tools have two modes: open mode and close mode. When the supra mitral devices are inside the catheter they are attached to the umbrella folded to its close mode. When the umbrella with the folded device on it emerges from the catheter above the mitral valve, the umbrella opens and the supra mitral device unfolds. The umbrella is configured for holding and adjusting the device in its final position. The umbrella is removed or detached after the supra mitral device is attached to the leaflets with the coupling elements.

Figure 7A:
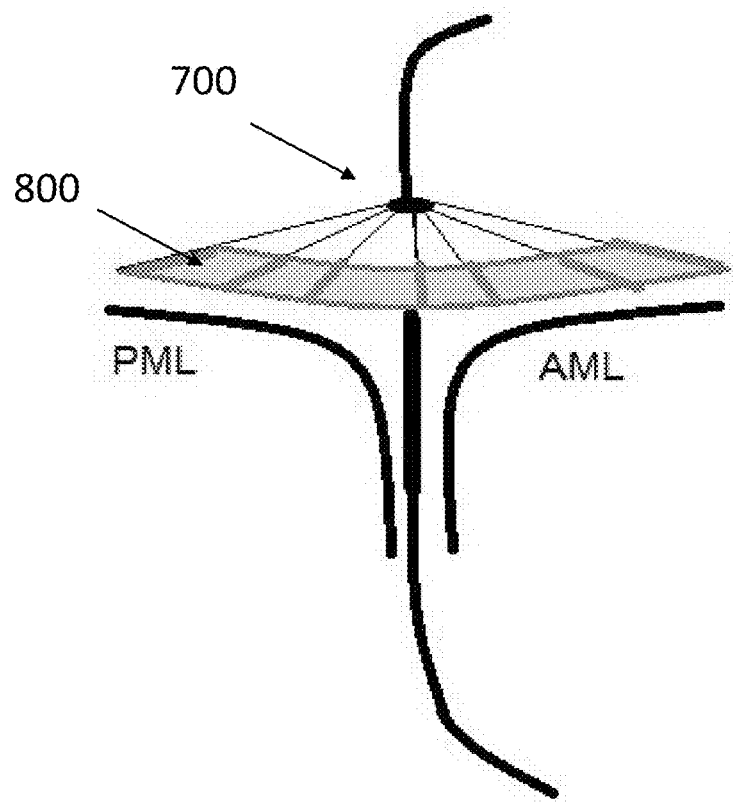
FIGS. 7A-L schematically illustrate "umbrella" type supra mitral device deployment tools, according to some embodiments.

FIG. 7A shows a deployment tool in a shape of an umbrella referred herein as a first umbrella deployment tool 700. First umbrella deployment tool 700 is configured to deploy/position and detach supra mitral device 800 (but may be applied with any other a supra mitral device, for example, but not limited to, supra mitral device 100, 100', 177, 178, 10, 20, 30, 40, 50 and 60 in FIGS. 1A-G and FIGS. 18-22) on the mitral valve. PML represents the posterior mitral leaflet and AML represents the anterior mitral leaflet. The radius of umbrella deployment tool 700 may be around 2 cm plus/minus 0.7 cm (covers the range of diameters of 3-5.4 cm, which will include most patients). The arms of umbrella deployment tool 700 provide positioning and penetration support.

Figure 7B:
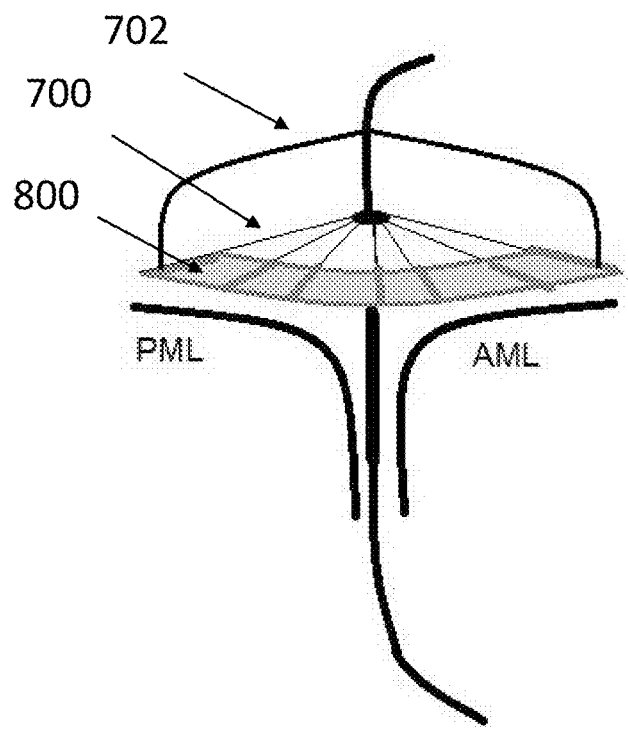

FIG. 7B shows umbrella deployment tool 700 and an attachment tool, also in a shape of an umbrella, referred to herein as a second umbrella attachment tool 702, which rides first umbrella deployment tool 700. Second umbrella attachment tool 702 is configured to release the coupling elements. Two first arms of second umbrella attachment tool 702 are illustrated here, not reaching the margin of supra mitral device 800, and are intended to release the coupling elements such that they penetrate the leaflet, not the annulus.

Figure 7C:
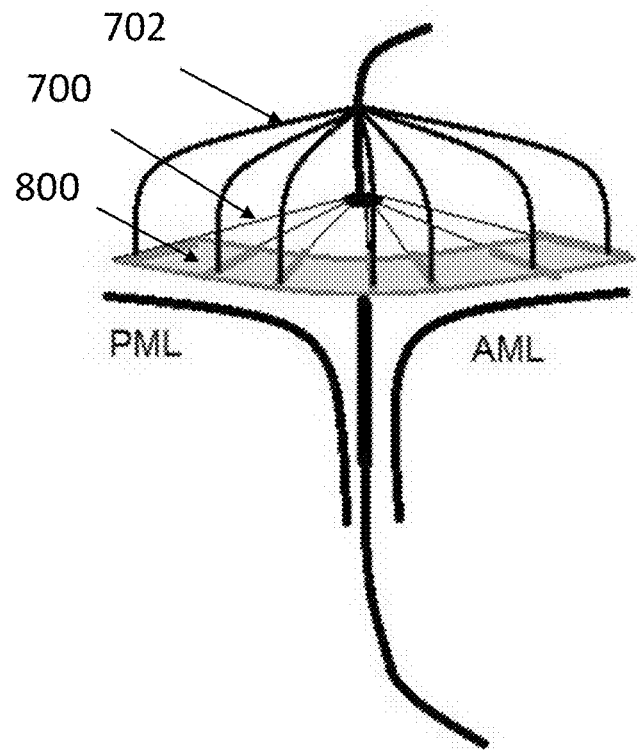

More arms, such as 4-12 for example, 6-8 arms, may be required for a peripheral line of arms (FIG. 7C).

Figure 7D:
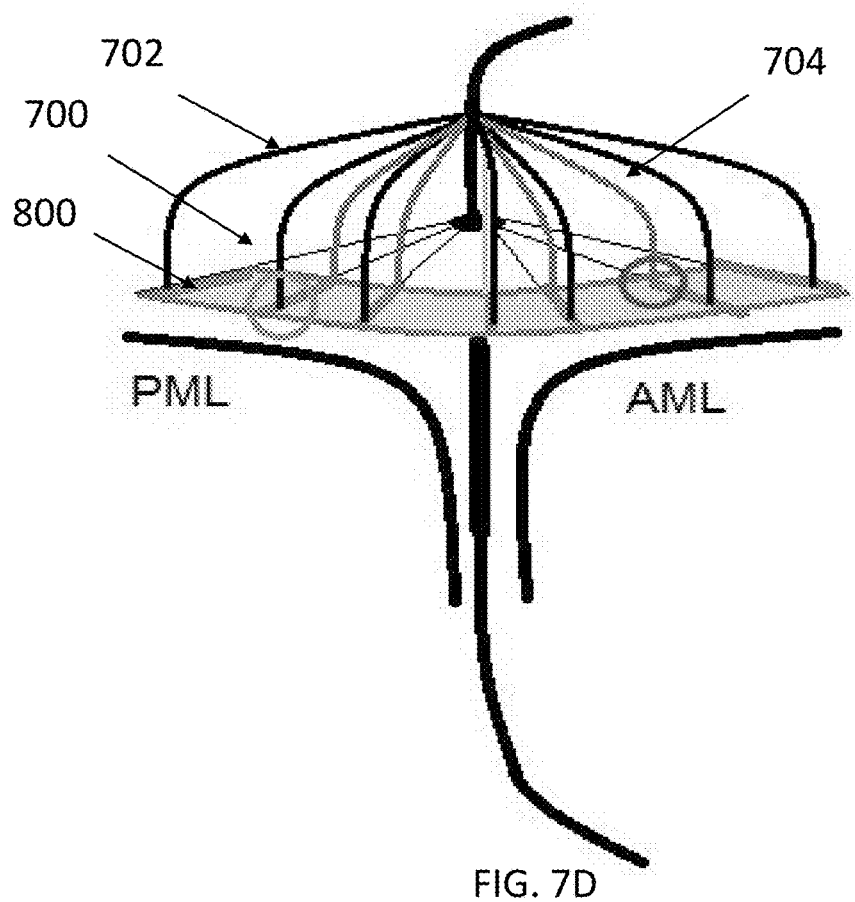
Figure 7E:
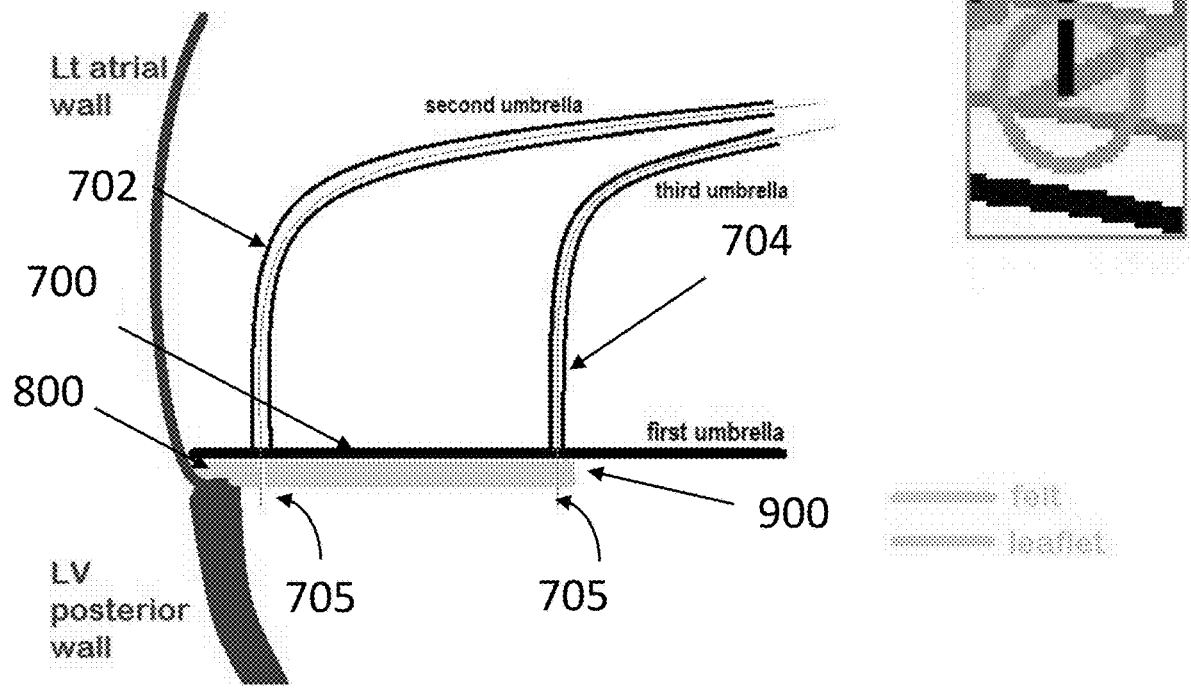

A third umbrella attachment tool 704 may then be added, having an inner line of arms, thus forming a triple umbrella structure (FIG. 7D, 7E). The arms of third umbrella attachment tool 704 are directed to an inner rim of supra mitral device 800 on the posterior mitral leaflet only (FIG. 7E).

Figure 7F:
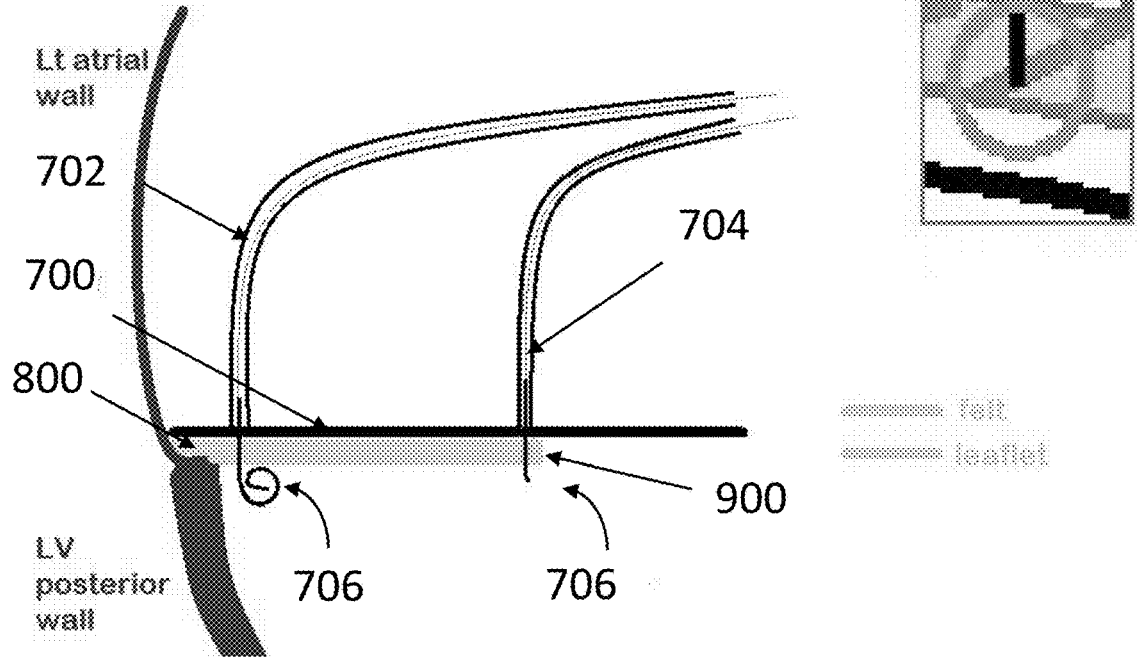

FIG. 7E demonstrates a blow-up of two of the coupling elements penetration sites marked in circles (in FIG. 7D). In the close-up views, it can be seen that the arms of the umbrellas are thin tubes, though which penetrating wires 705 are inserted to be replaced by coupling elements 706 connecting supra mitral device 800 to leaflet 900 (FIG. 7F).

Figure 7G:
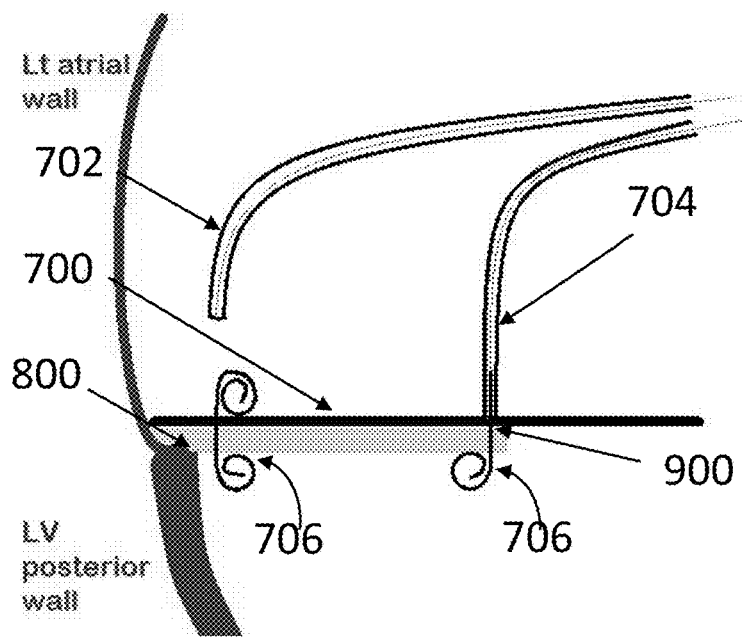
Figure 7G:
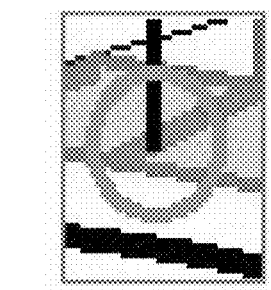

Once the peripheral coupling elements (such as coupling elements 706) are fully released by second umbrella attachment tool 702, the inner rim coupling elements are pushed in position by the arms of the third umbrella attachment tool 704 (FIG. 7G).

Figure 7H:
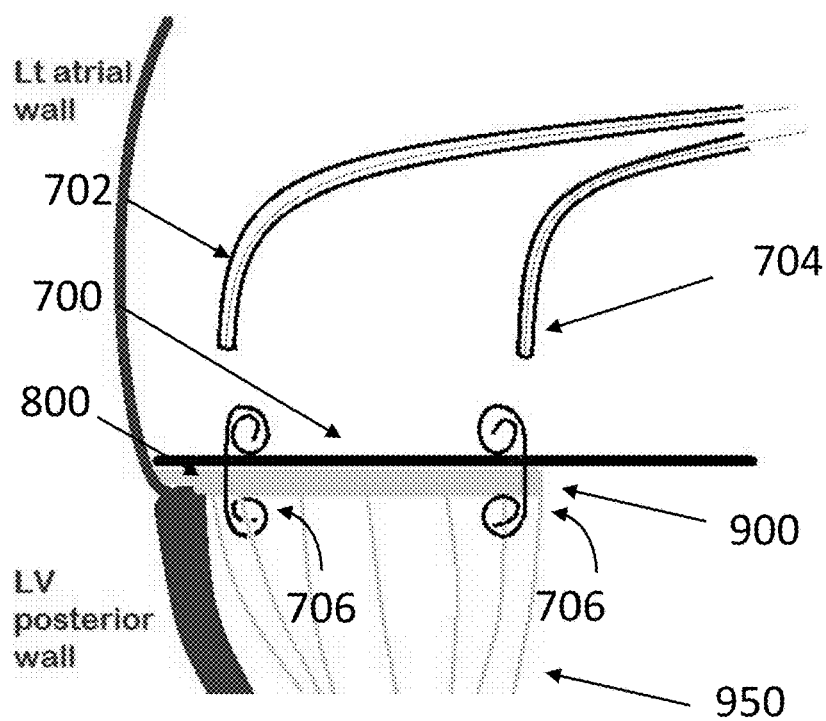
Figure 7H:
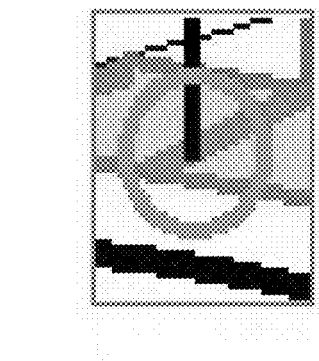
Figure 7I:
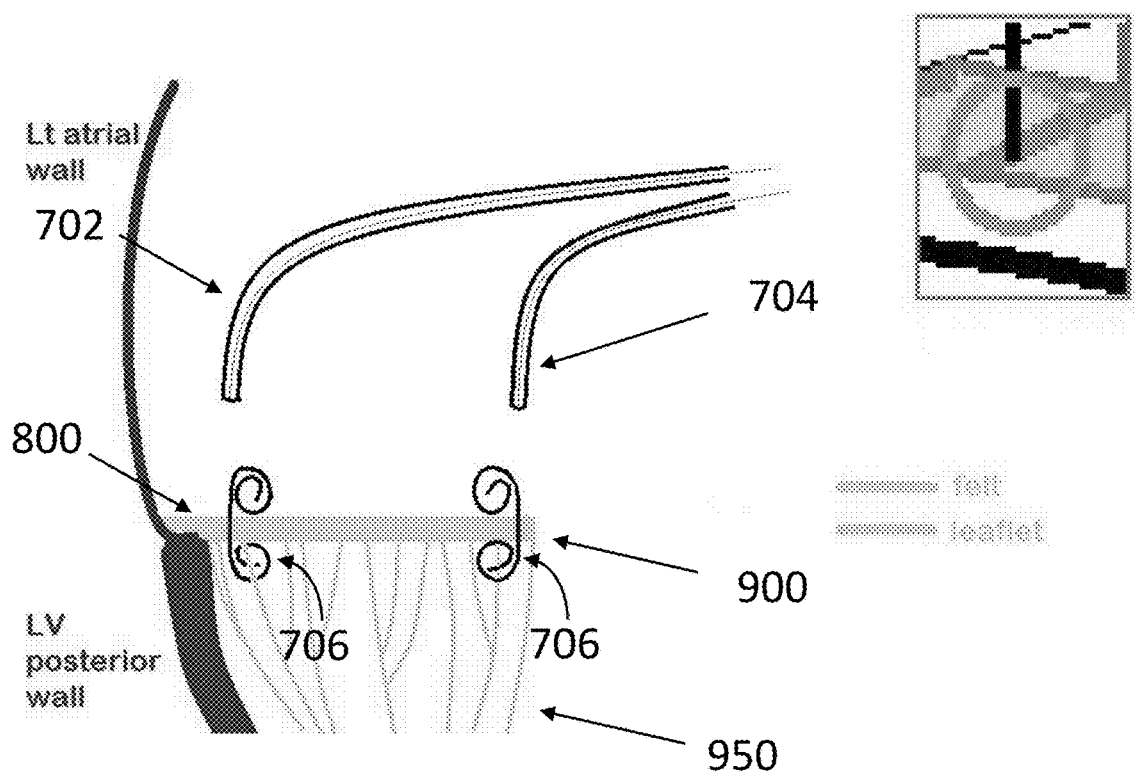

Once outer and inner rim coupling elements (such as coupling elements 706) are in place, second and third umbrella attachment tools (702 and 704, respectively) are released (FIG. 7H). The chords 950 are illustrated, and one can note they are essentially parallel to coupling elements 706. In the last step (FIG. 7I), supra mitral device 800 is detached from first umbrella deployment tool 700, anchored in place by coupling elements 706. First umbrella deployment tool 700 is then removed.

Figure 7J:
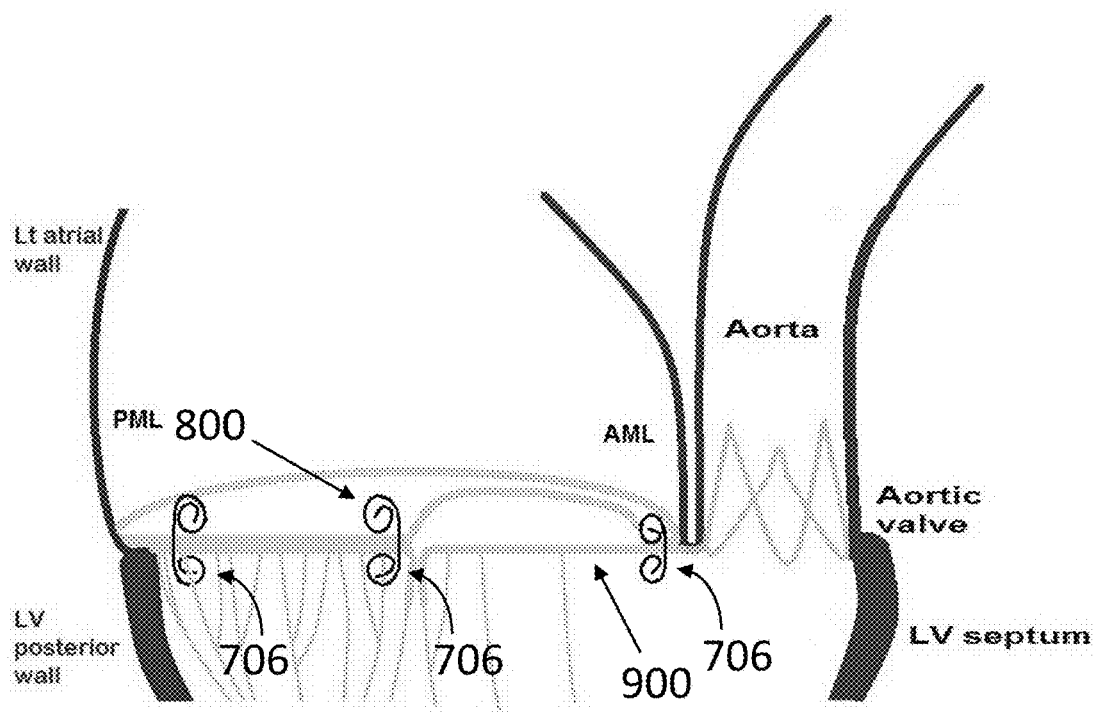

The three umbrellas are removed, supra mitral device 800 is in place, safely coupled to the mitral valve by coupling elements 706 (FIG. 7J). It can be seen that the anterior leaflet's movement is not jeopardized while the posterior leaflet's movement is minimized to nullified/abolished.

Figure 7K:
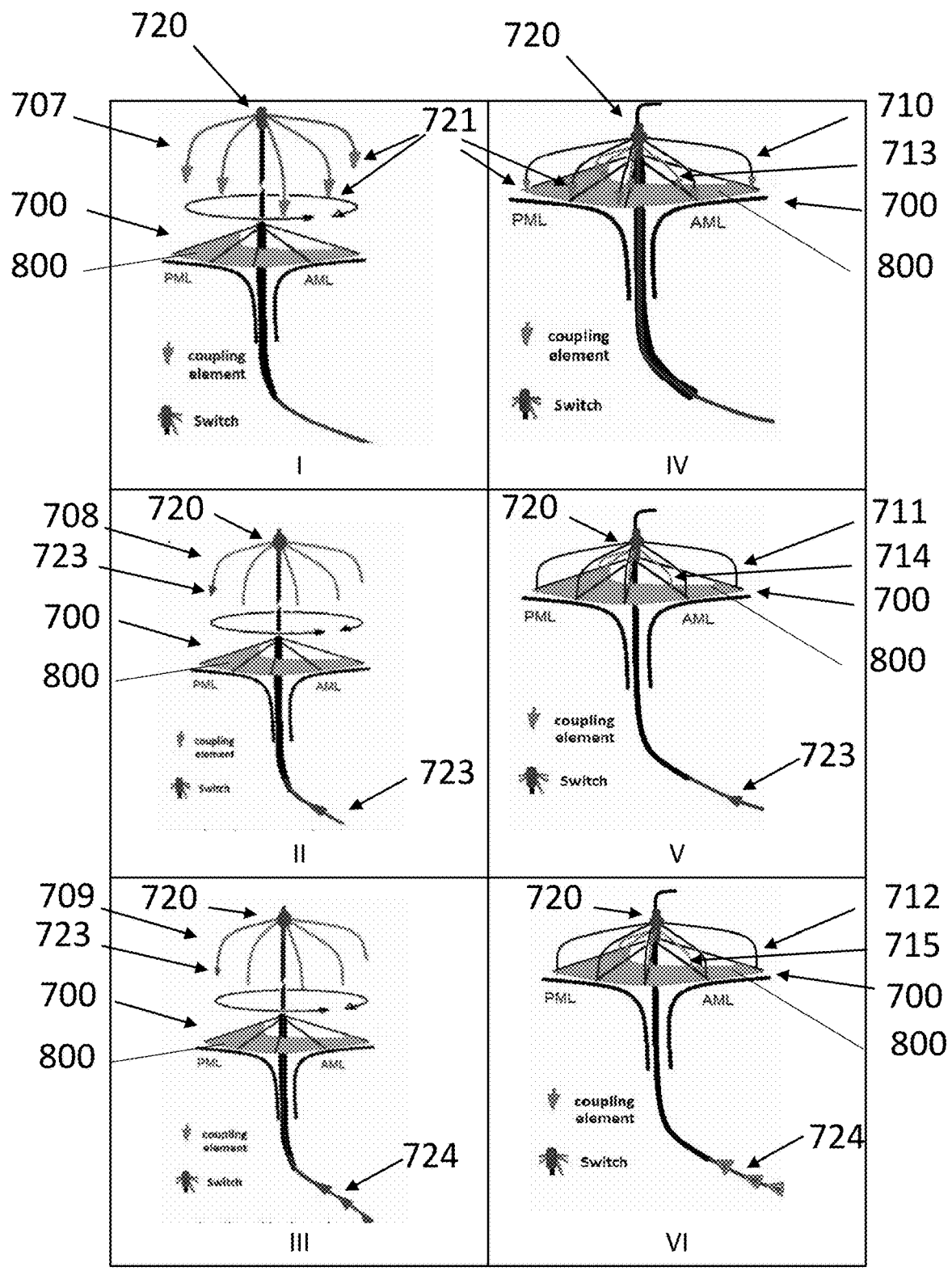

Reference is now made to FIG. 7K I-III, each schematically illustrating two separate umbrellas: first umbrella deployment tool 700 is configured to deploy, unfold and position supra mitral device 800 in place and second umbrella attachment tool 707, 708 and 709 respectively, is a separate tool (separate from first umbrella deployment tool 700), which has the same longitudinal axis as first umbrella deployment tool 700 and is configured for attaching supra mitral device 800 to the valve leaflet by introducing coupling elements through its arms. Each of the first and second umbrellas may be adjusted separately. The first and second umbrellas may be introduced through left Catheterization retrograde through the Aorta or Apical.

In second umbrella attachment tool 707 (FIG. 7K I) each arm has one or more preinserted coupling element 721. Second umbrella attachment tool 707 has (or is associated with) a switch 720 for controlling and selecting which arm to operate.

In second umbrella attachment tool 708 (FIG. 7K II) coupling elements 723 are directed one by one to each arm. Second umbrella attachment tool 708 has (or is associated with) a switch 720 for controlling and selecting which arm to operate.

In second umbrella attachment tool 709 (FIG. 7K III) coupling elements 723 are directed by a coupling cartridge 724 one by one to each arm. Second umbrella attachment tool 709 has (or is associated with) a switch 720 for controlling and selecting which arm to operate. Switch 720 is further configured to direct coupling cartridge 724 to a different umbrella arm each time. Coupling cartridge 724 may include a plurality of separated coupling elements (such as coupling elements 723) or a wire from which coupling elements (such as coupling elements 723) are produced (e.g., cut).

Reference is now made to FIG. 7K IV-VI, each schematically illustrating a composite triple umbrella including: first umbrella deployment tool 700 is configured to deploy, unfold and position supra mitral device 800 in place, a second umbrella attachment tool 710, 711 and 712 respectively, configured for attaching supra mitral device 800 to the valve leaflet by introducing coupling elements through its arms (to the posterior and anterior leaflets along their outer margins), and a third umbrella attachment tool 713, 714 and 715 respectively, configured for attaching supra mitral device 800 to the valve leaflet by introducing coupling elements through its arms (to the posterior leaflet along its inner margins). The triple umbrellas may be introduced through left Catheterization retrograde through the Aorta or Apical.

In second umbrella attachment tool 710 and third umbrella attachment tool 713 (FIG. 7K IV) each arm has one or more preinserted coupling element 723 and has (or is associated with) a switch 720 for controlling and selecting which arm to operate.

In second umbrella attachment tool 711 and third umbrella attachment tool 714 (FIG. 7K V) coupling elements 723 are directed one by one to each arm. Second umbrella attachment tool 711 and third umbrella attachment tool 714 have (or are associated with) a switch 720 for controlling and selecting which arm to operate.

In second umbrella attachment tool 712 and third umbrella attachment tool 715 (FIG. 7K VI) coupling elements 723 are directed by coupling cartridge 724 one by one to each arm. Second umbrella attachment tool 712 and third umbrella attachment tool 715 have (or are associated with) switch 720 for controlling and selecting which arm to operate. Switch 720 is further configured to direct coupling cartridge 724 to a different umbrella arm each time. Coupling cartridge 724 may include a plurality of separated coupling elements (such as coupling elements 723) or a wire from which coupling elements (such as coupling elements 723) are produced (e.g., cut).

Figure 7L:
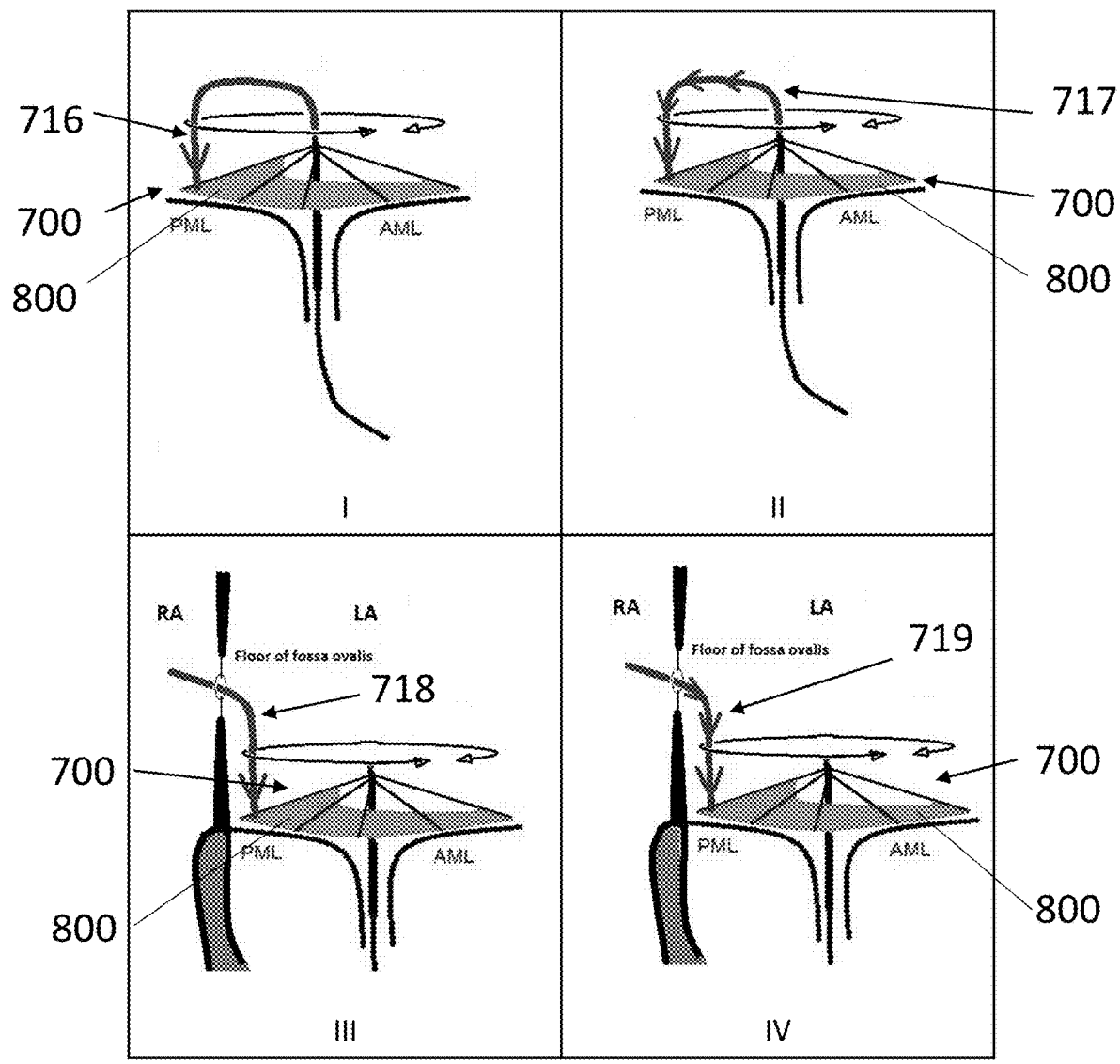

Reference is now made to FIG. 7L I-IV, each schematically illustrates a first umbrella deployment tool 700 configured to deploy, unfold and position supra mitral device 800 in place, and single arm attachment tools 716, 717, 718 and 719 respectively, configured for attaching supra mitral device 800 to the valve leaflet by introducing coupling elements through its arm.

As shown in FIG. 7L I-II both first umbrella deployment tool 700 and respective single arm attachment tools 716 and 717 are inserted on the same axis by left sided retrograde procedure through the aorta or apically. Single arm attachment tool 716 (FIG. 7L I) is configured to deploy a single coupling element at a time (one by one) and thus attach supra mitral device 800 to the mitral leaflets all around. Single arm attachment tool 717 (FIG. 7L II) has a cartridge of multiple coupling elements for one by one insertion and is thus configured to attach supra mitral device 800 to the mitral leaflets all around.

As shown in FIG. 7L III-IV first umbrella deployment tool 700 is inserted by left sided retrograde procedure through the aorta or apically, while respective single arm attachment tools 718 and 719 are introduced through right catheterization. Single arm attachment tool 718 (FIG. 7L III) is configured to deploy a single coupling element at a time (one by one) and thus attach supra mitral device 800 to the mitral leaflets all around. Single arm attachment tool 719 (FIG. 7L IV) has a cartridge of multiple coupling elements for one by one insertion and is thus configured to attach supra mitral device 800 to the mitral leaflets all around.

It is noted that, in accordance with some embodiments, the deployment/attachment tools presented in FIGS. 7A-L may be used for deploying any one of the supra mitral devices disclosed herein, for example, but not limited to, supra mitral device 100, 100', 177, 178, 10, 20, 30, 40, 50 and 60 in FIGS. 1A-G and FIGS. 18-22. In accordance with additional/alternative embodiments, the deployment tools presented in FIGS. 7A-L may be used for deploying any supra mitral devices.

Figure 8:
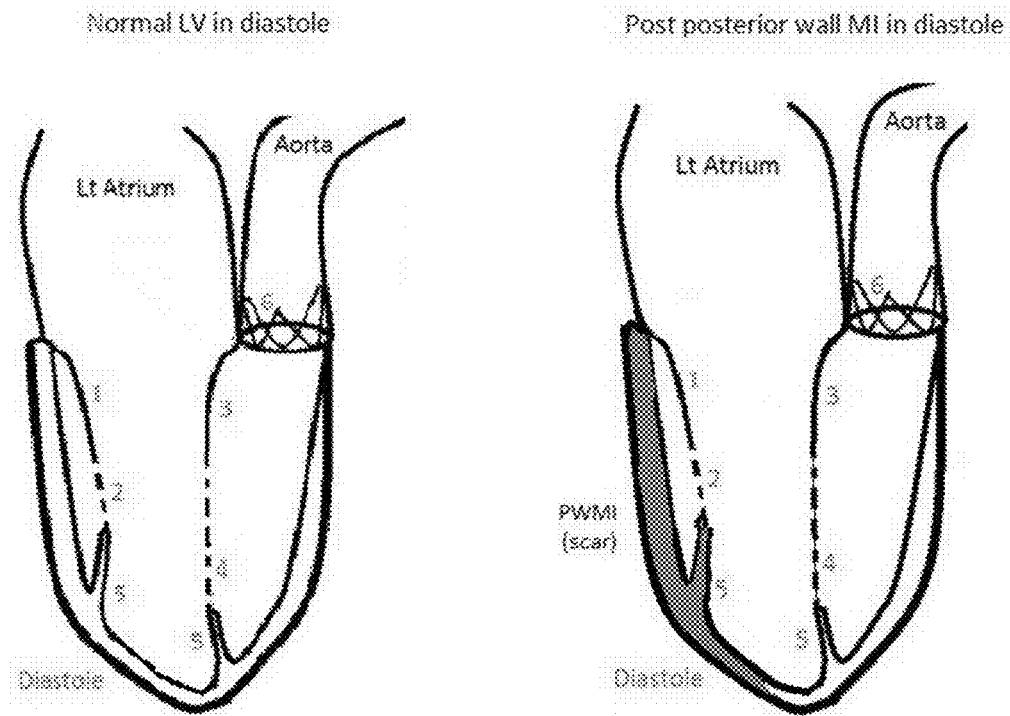
FIG. 8 schematically illustrates the mitral valve region and the LV after posterior wall myocardial infarction (MI) in diastole.

It is also noted that, in accordance with some embodiments, the any one of the coupling/coupling elements presented herein (for example, but not limited to, in FIGS. 2-6) may be used with any one of the deployment tools presented herein (for example, but not limited to, in FIGS. 7 A-L) for deploying any one of the supra mitral devices disclosed herein, for example but not limited to supra mitral device 100, 100', 177, 178, 10, 20, 30, 40, 50 and 60 in FIGS. 1A-G and FIGS. 18-22. In accordance with additional/alternative embodiments, the deployment tools presented in FIGS. 7A-L may be used for deploying any supra mitral devices. Transcatheter Mitral Valve Repair (TMVRr) for Functional Mitral Regurgitation (FMR):

Reference is now made to FIG. 8-FIG. 15, which show the problems related to FMR and to the existing attempts to solve these problems. FIG. 8 schematically illustrates the mitral valve region with normal LV (left) and after posterior wall myocardial infarction (MI) (right) in diastole. It can be seen that after posterior wall MI with scarring of the posterior wall, the mitral valve seems rather normal on diastole.

Figure 9:
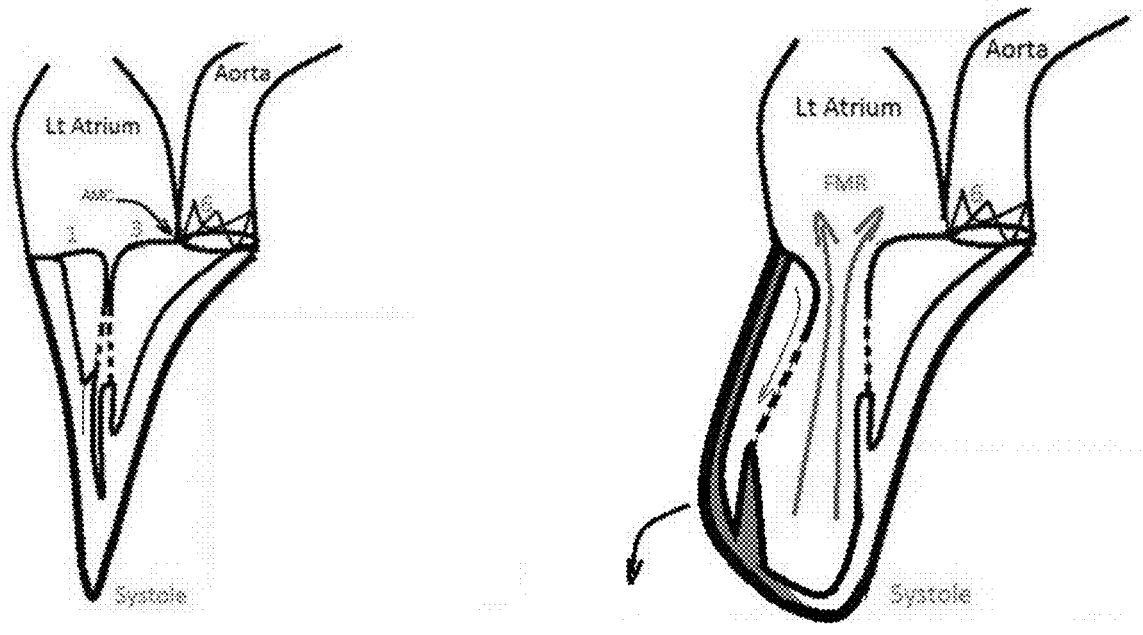
FIG. 9 schematically illustrates the mitral valve region and the LV after posterior wall MI in systole.

FIG. 9 schematically illustrates the mitral valve region with normal LV contraction with normal MV coaptation (left)—good coaptation of PML with the AML is achieved; and Abnormal LV contraction after posterior wall MI (right) in systole. It can be seen that the "normal appearing mitral valve" is not effective: The failure of the posterior infarcted LV wall to contract, and even more, bellow in the opposite direction, causes a pull-down effect on the posterior leaflet (thin arrow), generating MR. This type of MR is called functional MR (FMR).

Figure 10:
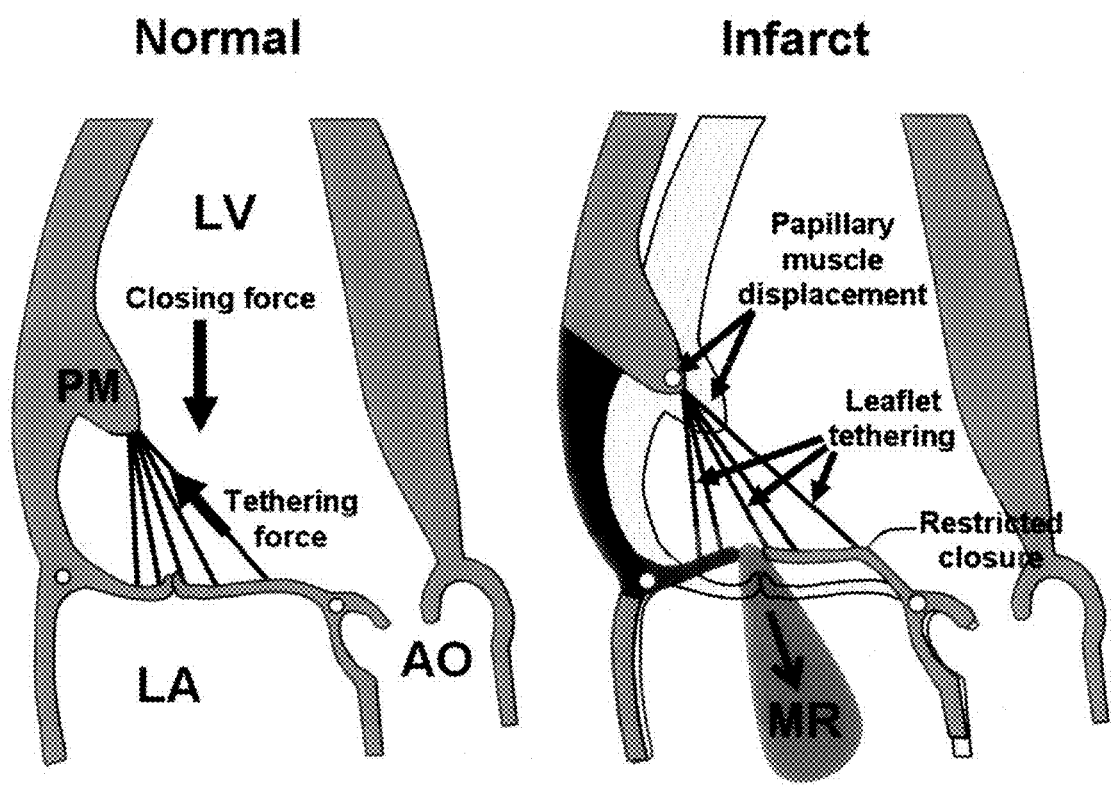
FIG. 10 schematically illustrates papillary muscle displacement post MI (R. A. Levine, E. Schwammenthal: *Circulation*. 2005; 112:745-758)

The following depict the respective parts in the valve region:
1—Posterior mitral leaflet;
2—Chordae;
3—Anterior mitral leaflet;
4—Chordae;
5—Papillary muscles; and
6—Aortic valve
AMC—Aortic-mitral continuity FIG. 10 schematically illustrates papillary muscle displacement and posterior leaflet tethering post MI (right) in comparison to normal papillary muscle (left). Tethering may involve the anterior leaflet, to a lesser extent (R. A. Levine, E. Schwammenthal: *Circulation.* 2005; 112:745-758).

Figure 11:
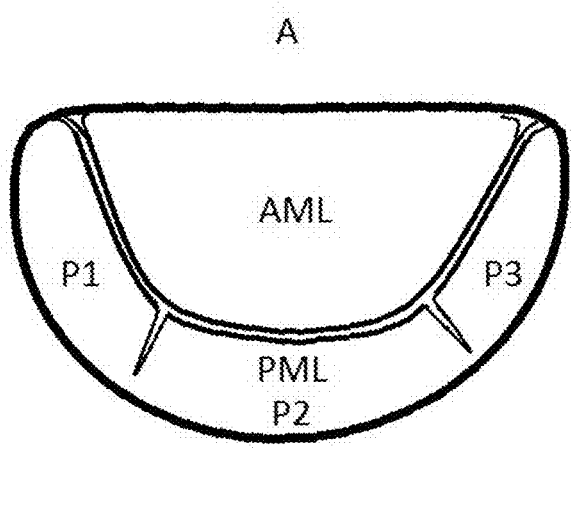
FIG. 11 schematically illustrates a view of the mitral valve from the LA in systole.
Figure 11:
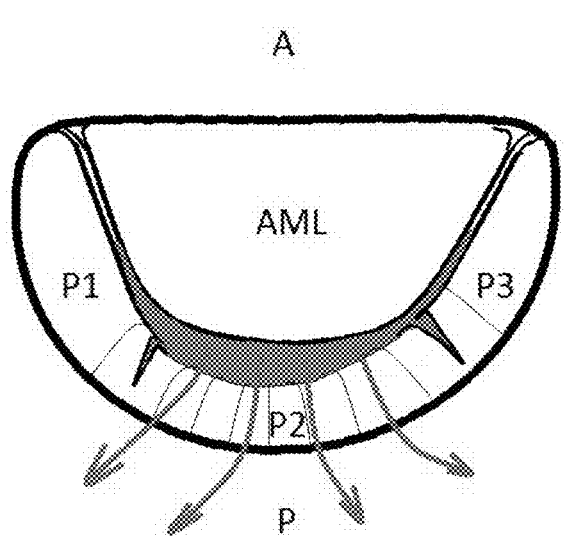

FIG. 11 schematically illustrates a view of the mitral valve from the LA in systole in heart post posterior MI (right), in comparison to normal mitral valve with normal coaptation (left). In heart post posterior MI (right) one can notice, pull-down (tethering) of the posterior leaflet mostly, causes mal-coaptation and MR. Posterior wall MI with abnormal contraction/movement of the posterior wall and papillary muscles, causes pull-down on segments of the posterior leaflet. This is most evident on P2 and adjacent parts. In a normal mitral valve (left) one can notice good coaptation with no MR.

Figure 12:
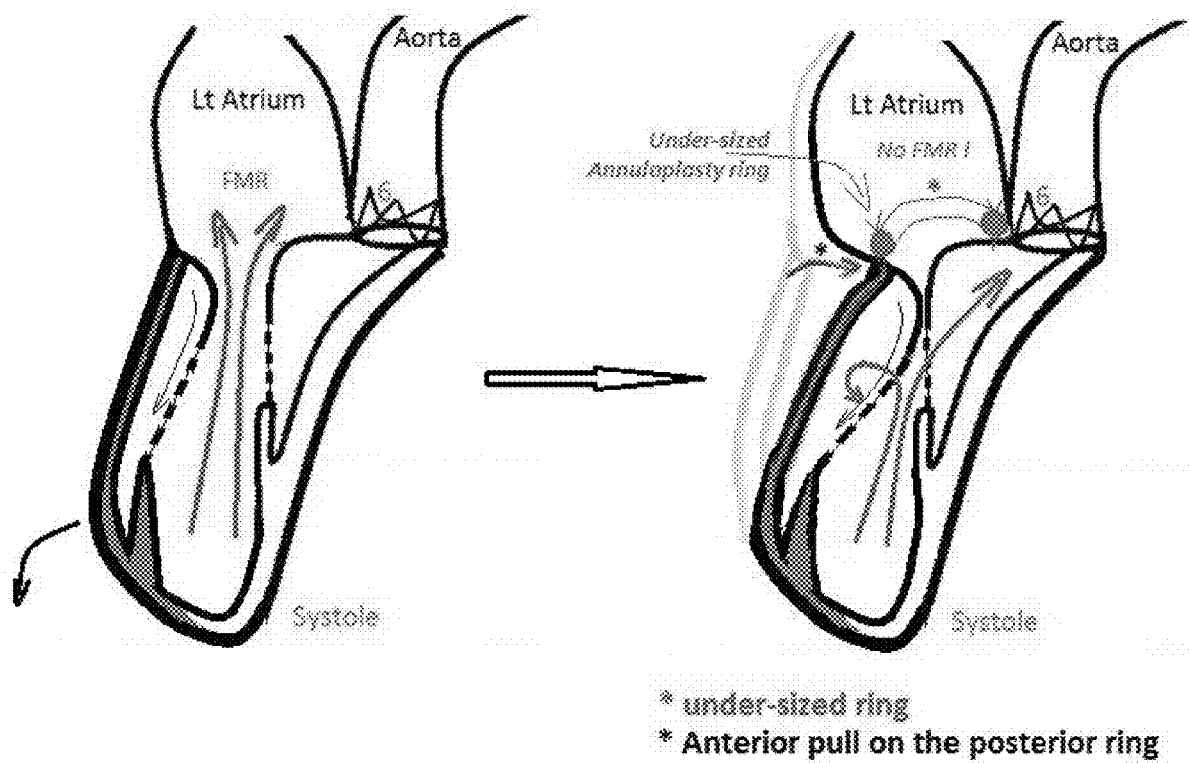
FIG. 12 schematically illustrates an undersized ring repair according to the prior art (Steven Bolling)

FIG. 12 schematically illustrates an undersized ring repair according to the prior art (Steven Bolling). Recurrent mitral regurgitation is demonstrated after annuloplasty for functional ischemic mitral regurgitation as evident, for example by the following publication: "During the first 6 months after repair, the proportion of patients with 0 or 1+ mitral regurgitation decreased from 71% to 41%, whereas the proportion with 3+ or 4+ regurgitation increased from 13% to 28%." (McGee E C, Gillinov A M, Blackstone E H, Rajeswaran J, Cohen G, Najam F, Shiota T, Sabik J F, Lytle B W, McCarthy P M, Cosgrove D M J Thorac Cardiovasc Surg 2004; 128: 916). Namely, after a seemingly successful FMR surgical repair with under-sized ring, in follow-ups, the MR returned/increased significantly is just few months. This is as the LV remodeling continues, the LV dilates more and more and the down-tethering of the mitral leaflet gets even worse ("LV remodeling is a moving target"). This further reduces mitral leaflet coaptation, and MR increases. This report shows that under-sized ring approach has bad intermediate and long-term results.

Figure 13:
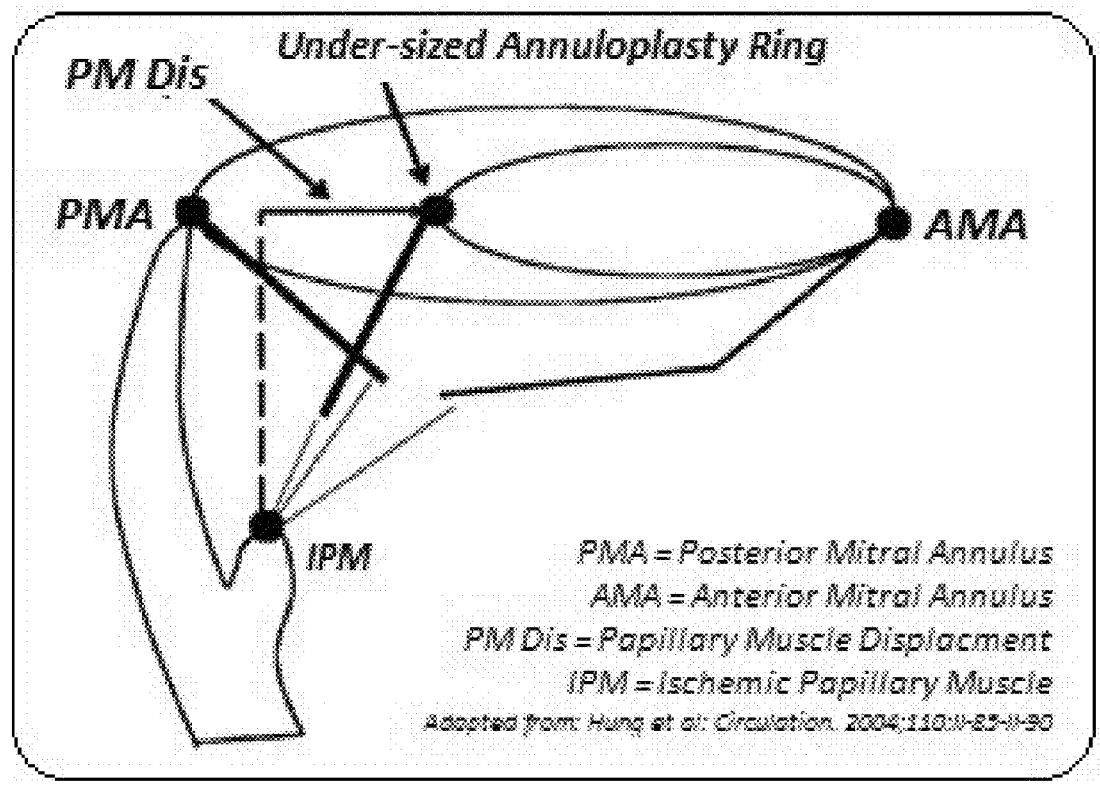
FIG. 13 schematically illustrates an undersized ring repair late MR recurrence.

FIG. 13 schematically illustrates the mechanism of recurrent ischemic mitral regurgitation after annuloplasty. The LV remodeling is continued as a moving target (Judy Hung et al. Circulation. 2004; 110:II-85). "Undersized annuloplasty corrects annular dilatation but worsens leaflet tethering and flattening") J. Daniel Robb et al.: Eur J Cardiothorac Surg. 2011 December; 40(6):1501 (Experimental)) "Posterior leaflet augmentation and less-extreme annular undersizing would relieve tethering and increase leaflet curvature".

Figure 14:
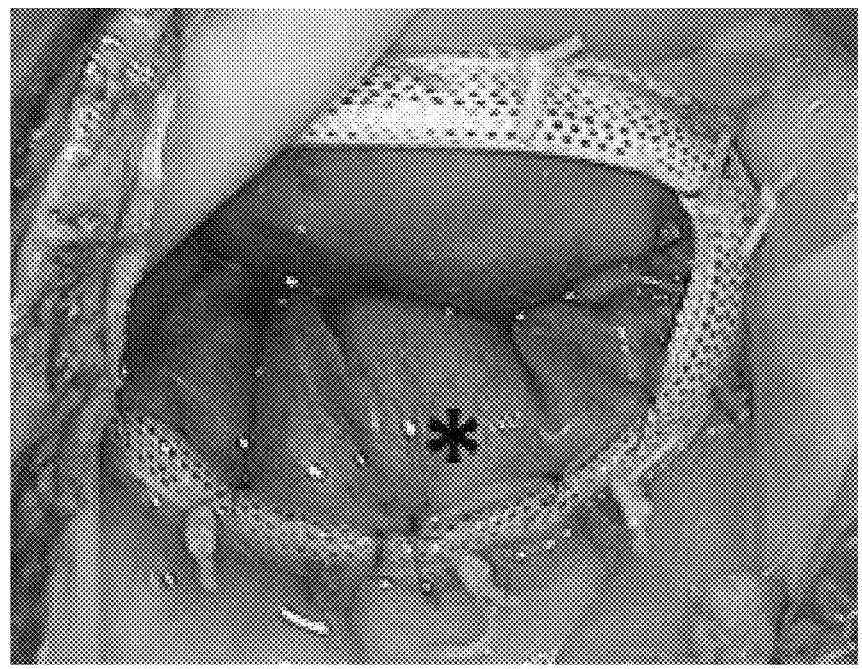
FIG. 14 schematically illustrates an intra-operative picture of prior art posterior leaflet augmentation for FMR in human patients (S. Mitsuyama et al.: Mitral Valve Repair by Posterior Leaflet Augmentation for Ischemic Mitral regurgitation. In: AATS Mitral Conclave; Breakout Session 9: Surgery for Ischemic Mitral Regurgitation, Thursday, Apr. 27, 2017)

FIG. 14 schematically illustrates an intra-operative picture of prior art posterior leaflet augmentation for FMR in human patients (S. Mitsuyama et al.: Mitral Valve Repair by Posterior Leaflet Augmentation for Ischemic Mitral regurgitation. In: AATS Mitral Conclave; Breakout Session 9: Surgery for Ischemic Mitral Regurgitation, Thursday, Apr. 27, 2017). The mean implanted annuloplasty ring size was 32.4±1.5 mm. All that is seen as the posterior leaflet (*) is the pericardial augmentation patch. What seems to be the posterior leaflet in this picture, marked with a star, is not a mitral leaflet at all: it is the pericard used for posterior leaflet augmentation. It coapts to the anterior leaflet (the top of the picture), which is a true leaflet.

Figure 15:
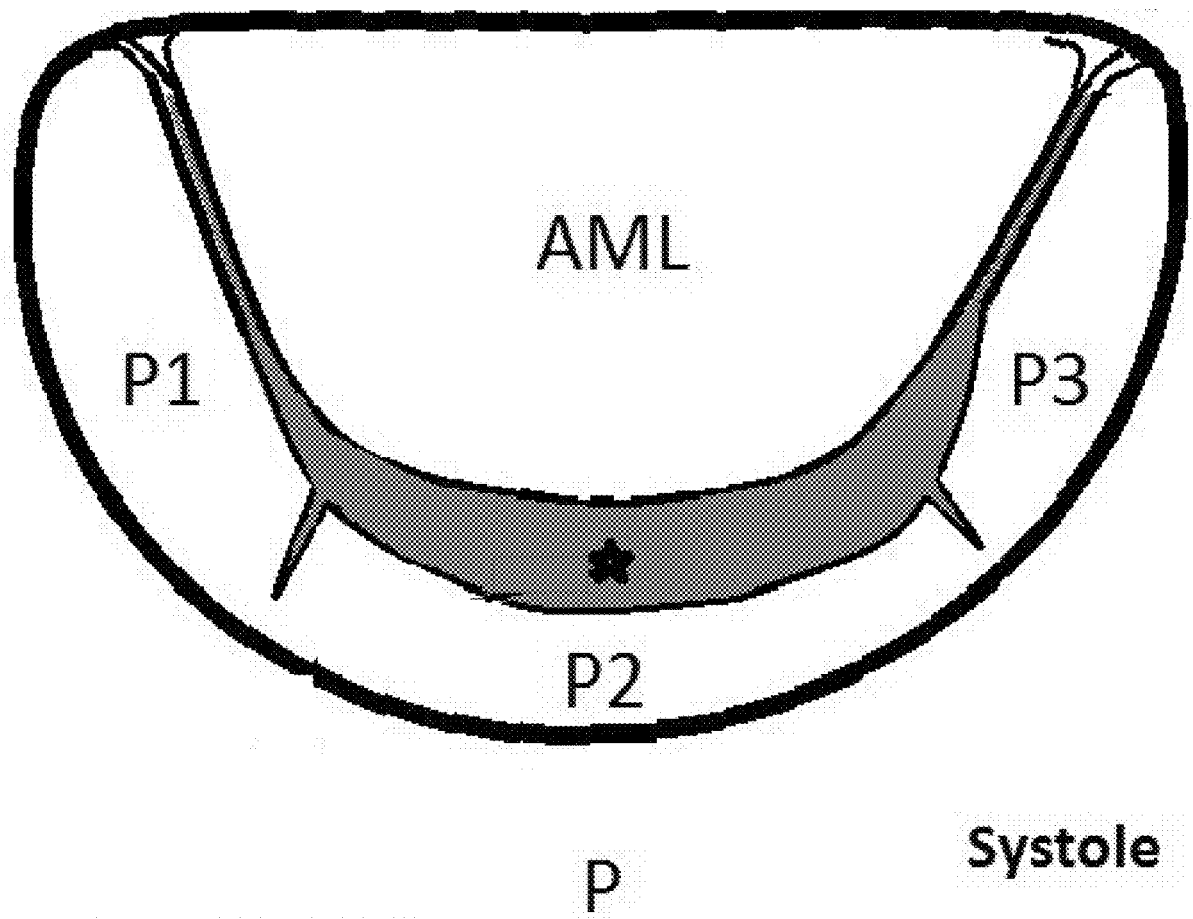
FIG. 15 illustrates a schematic view of the mitral valve from the LA in systole FMR.

FIG. 15 illustrates a schematic view of the mitral valve from the LA in systole FMR. As demonstrated (in the region depicted by the symbol "*"), the tethered down PML in FMR generates mal-coaptation of the anterior and posterior leaflets. Areas of the PML are tethered down in FMR, while P2 and p3 are not affected (or minimally affected). An under-sized ring has inherent drawbacks, it increases posterior leaflet tethering and MR often returns ("Continued LV Remodeling as a Moving Target" Judy Hung et al. Circulation. 2004; 110:II-85).

There is thus provided herein, in accordance with some embodiments, a supra mitral device and method for mitral valve repair in a subject suffering from FMA. The device includes a supra mitral device having essentially annular D-shape with an eccentric opening, such that a posterior section of the supra mitral device is wider than an anterior section of the supra mitral device, the posterior section of the supra mitral device configured for coverage and attachment to essentially all of the posterior leaflet of the mitral valve and (significantly) overlap at least a portion of the anterior leaflet of the mitral valve, thereby preventing and/or reducing mitral regurgitation, wherein the section of the posterior section of the supra mitral device which is configured to cover the posterior leaflet is made of a pliable material, adapted to stiffen after implantation of the device and wherein the part of the posterior section of the supra mitral device, which is configured to overlap at least a portion of the anterior leaflet is made of a softer material than the rest of the supra mitral device.

According to some embodiments, the supra mitral device is configured for coupling to the circumference of the mitral valve, and additionally for coupling to P1 and P3 leaflets. Further LV remodeling causes stronger tethering, which then effects P1 and P3 more and more, pulling the augmented posterior leaflet down, thus preserving its coaptation with the anterior leaflet.

Figure 16:
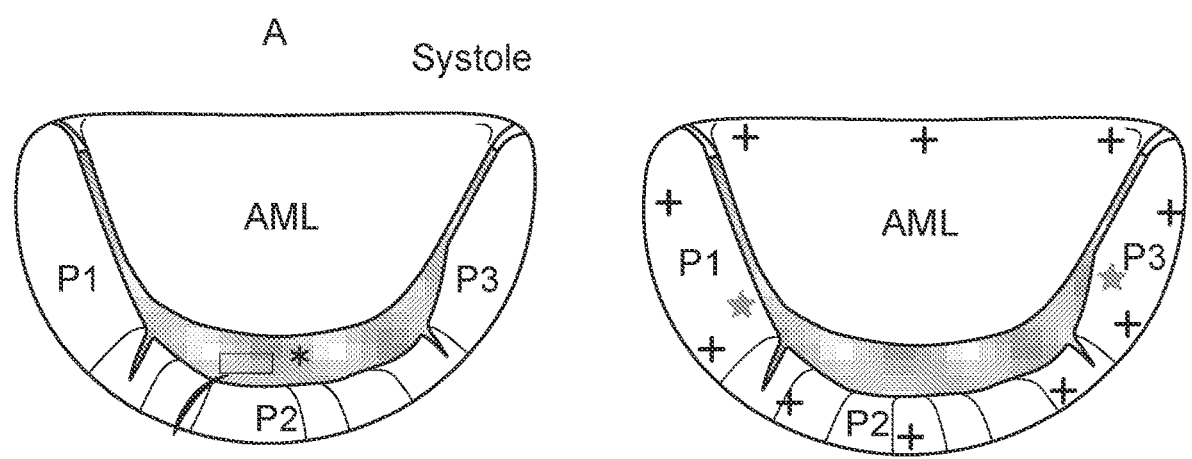
FIG. 16 schematically illustrates a supra mitral device and the coupling thereof (marked by + and *), according to some embodiments.
Figure 17:
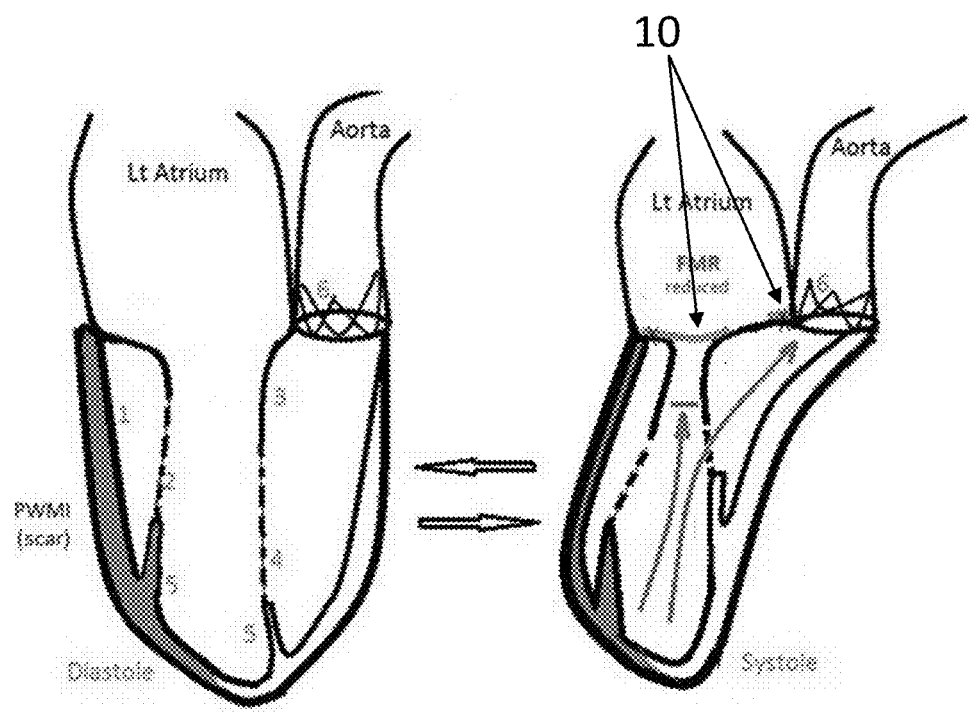
FIG. 17 schematically illustrates the supra mitral device used in FMR, according to some embodiments.
Figure 18:
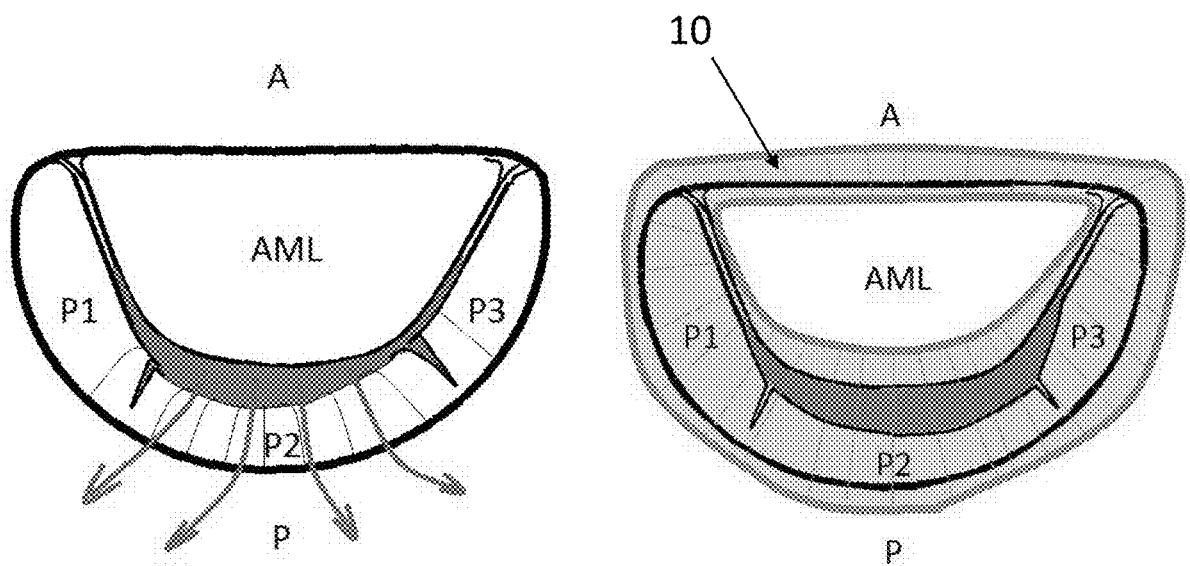
FIG. 18 schematically illustrates the supra mitral device for FMR, according to some embodiments.
Figure 19:
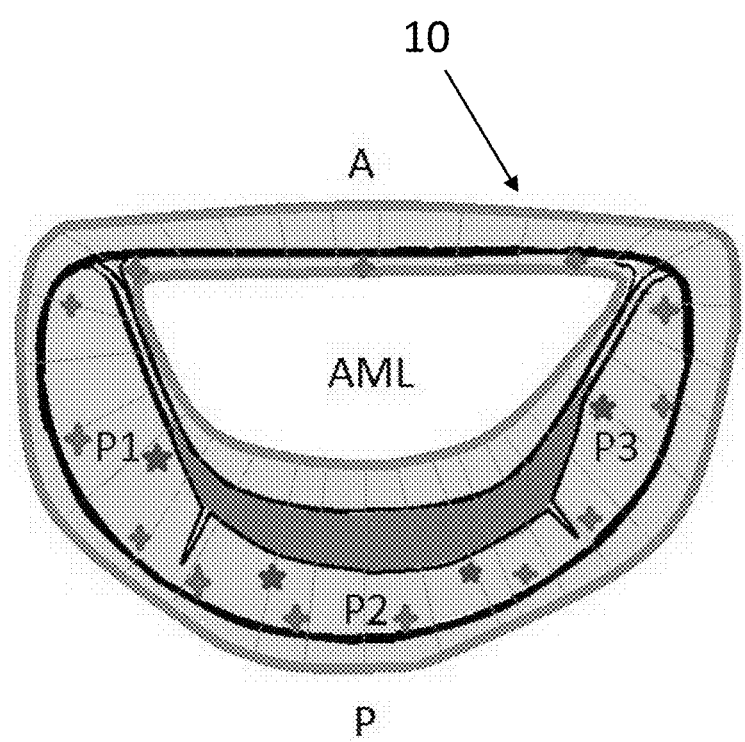
FIG. 19 schematically illustrates the supra mitral device for FMR and coupling thereof, according to some embodiments.

Advantageously, this supra mitral device, according to some embodiments, does not involve annuloplasty and thus avoids an increase of the posterior leaflet tethering. Utilizing the posterior leaflet augmentation supra mitral device, according to some embodiments, the problem of continued LV remodeling and increased tethering, which is more prominent in the posterior leaflet is prevented or at least mitigated. According to some embodiments, the supra mitral device is coupled to the mitral leaflet itself along its perimeter mostly, with extra pins on P1 and P3, the less tethered segments of the posterior mitral leaflet. FIG. 16 schematically illustrates the supra mitral device and the coupling thereof (marked by + and *), according to some embodiments. The coupling of the supra mitral device takes advantage of the fact that the tethering is not equally spread throughout the leaflets. The figure on the left shows a heart post posterior MI. As can be seen, pull-down (tethering) of the posterior leaflet, causes mal-coaptation and MR. The tethering of the PML leaves areas can be seen with no to minimal pull-down in P1 and P3, and the peripheral rim of P2. The tethering is maximal at the posterior side, much less in P1 and P3, leaving landing site for the supra mitral device: the "+" signs represent the coupling of the supra mitral device to the peripheral rim of the valve and the stars present coupling on P1 and P3 inner margin, which adjust the height of the augmentation segment via the AML. FIG. 17 and FIG. 18 schematically illustrate the supra mitral device used in FMR, according to some embodiments. The supra mitral device 10 may have a shape similar to the shape of device 100 i.e., an essentially annular, D shape and an eccentric opening, the opening located such that a posterior (marked as "P") section of device 100 is wider than an anterior (marked as "A") section of device 100. A difference, compared to device 100, is that device 10 has a wider posterior part, which overlaps significantly the anterior mitral leaflet. FIG. 19 schematically illustrates the supra mitral device 10 for FMR and coupling (marked by "*" and "+" signs) thereof, according to some embodiments. A key principle in coupling the device in FMR, according to some embodiments, are the coupling to P1 and P3 whose pull-down is minimal, and thus the support to the free anterior margin of the posterior part of the device is enhanced.

Figure 20:
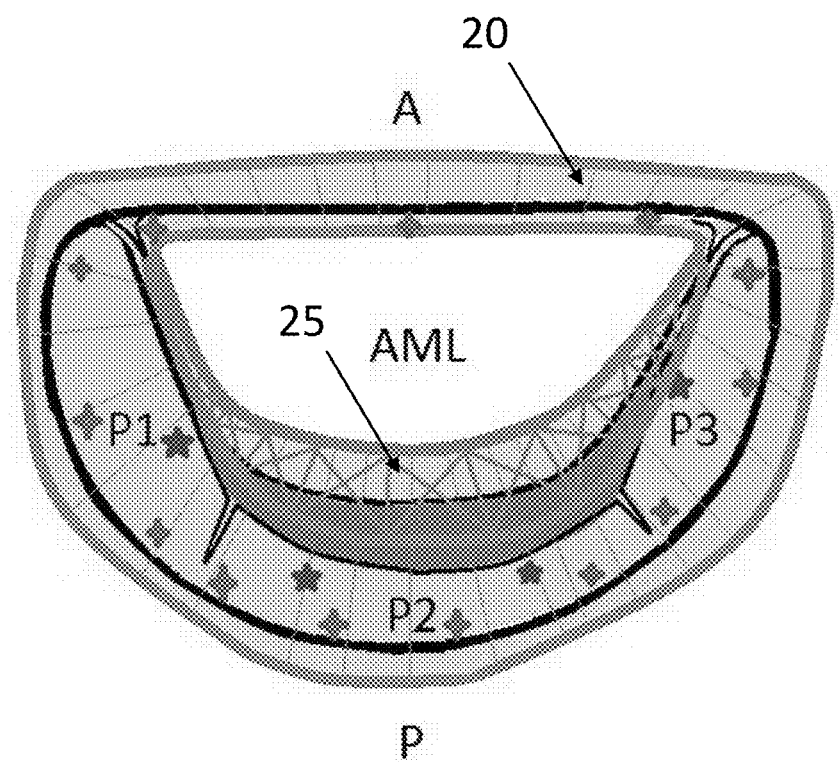
FIG. 20 schematically illustrates a supra mitral device for FMR and coupling thereof, according to some embodiments.

FIG. 20 schematically illustrates supra mitral device 20 for FMR and coupling (marked by "*" and "+" signs) thereof, according to some embodiments. According to some embodiments, suspension 25 of the posterior part of supra mitral device 20 overlapping with the AML may be like of a semi-lunar cusp, with the surrounding attachment pins and device shape providing all around support, and the LV pressure compresses the AML against it.

According to some embodiments, suspension 25 of the device overlapping with the anterior mitral leaflet may be made of a softer (compared to the rest of the device) and atraumatic material.

Figure 21:
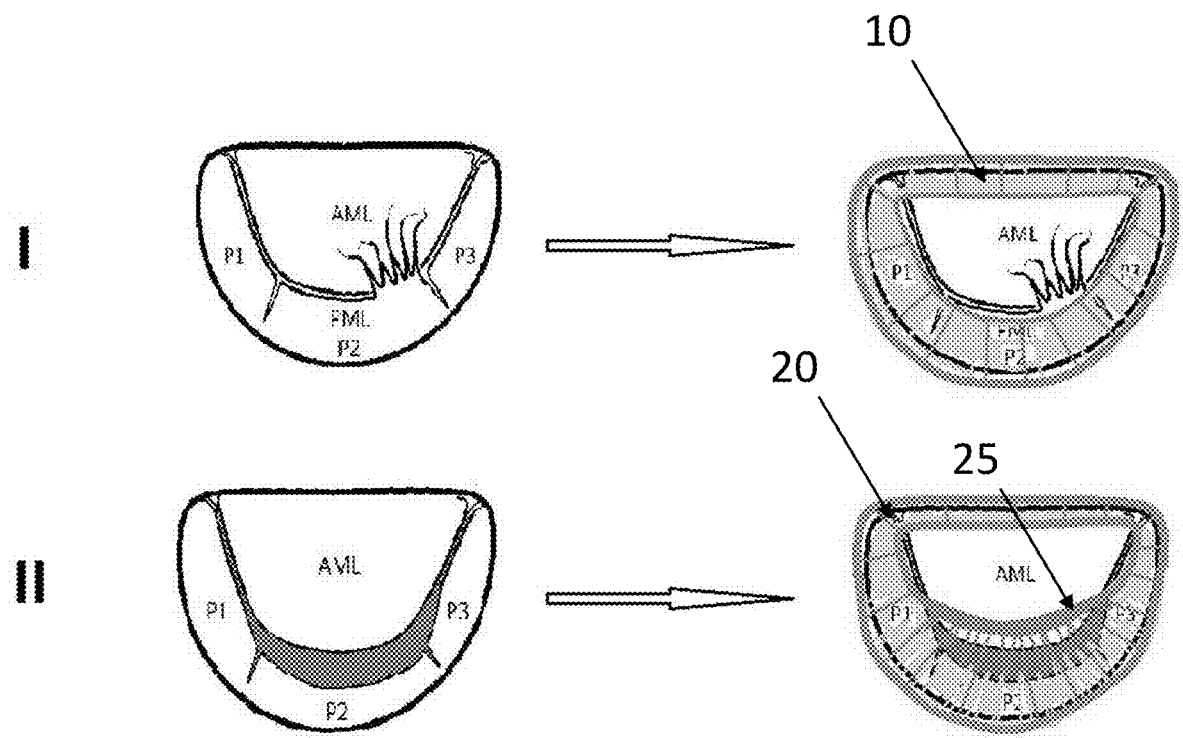
FIG. 21 schematically illustrates two types of supra mitral devices, according to some embodiments.

FIG. 21 schematically illustrates two types of devices, according to some embodiments:

I—supra mitral device 10, wherein the posterior part of the device does not overlap with the anterior leaflet. This type of device can be used, for example, for myxomatous mitral and chordae tear.

II—supra mitral device 20 having a suspension 25 and thus providing an overlap with the anterior leaflet. This type of device can be used in FMR.

Figure 22:
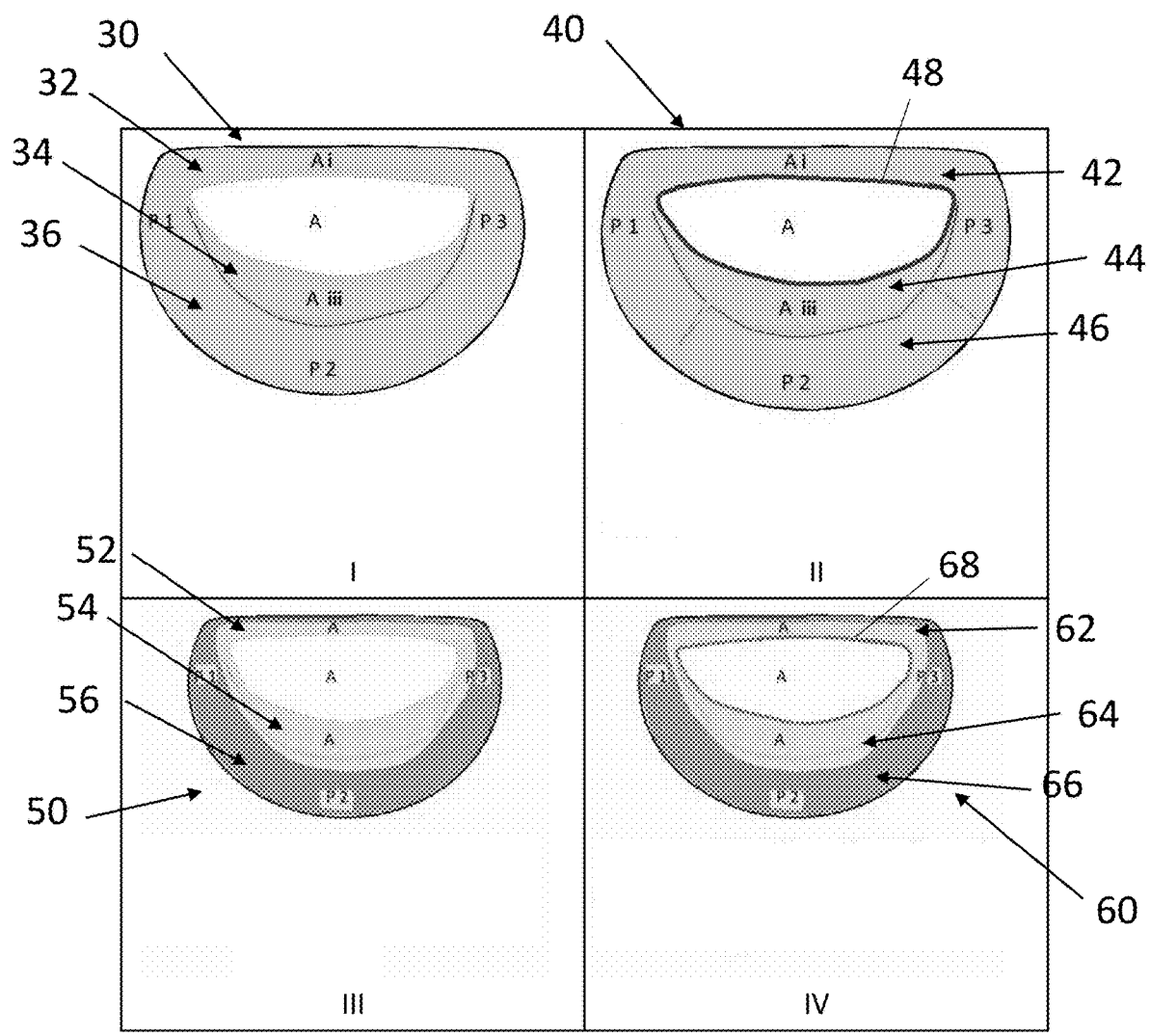
FIGS. 22 I-IV schematically illustrate different variations of supra mitral devices for use in FMR, according to some embodiments.

FIGS. 22 I-IV schematically illustrate different variations of supra mitral devices for use in FMR, namely devices 30, 40, 50 and 60, respectively, according to some embodiments. The supra mitral devices 30, 40, 50 and 60, have a shape similar to the shape of device 100 i.e., an essentially annular, D shape and an eccentric opening, the opening located such that a posterior (marked as "P") section of device 100 is wider than an anterior (marked as "A") section of device 100. A difference in supra mitral devices 30, 40, 50 and 60 compared to device 100, is that supra mitral devices 30, 40, 50 and 60 have a wider posterior part, which overlaps significantly the anterior mitral leaflet.

FIG. 22 I schematically shows a supra mitral device 30, having essentially a narrow anterior part 32, a posterior part 36 having an extension 34 between posterior part 36 and the opening of device 30; extension 34 is configured to cover (overlap with) the anterior mitral leaflet. Extension 34 may integrally be formed with posterior part 36. Extension 34 may integrally be contiguous with posterior part 36. Extension 34 may be connected to posterior part 36.

FIG. 22 II schematically shows a supra mitral device 40, having essentially a narrow anterior part 42, a posterior part 46 having an extension 44 between posterior part 46 and the opening of device 40; extension 44 is configured to cover (overlap with) the anterior mitral leaflet. Extension 44 may integrally be formed with posterior part 46. Extension 44 may integrally be contiguous with posterior part 46. Extension 44 may be connected to posterior part 46. Device 40 further comprises an enforcement member 48 extending along an inner edge of the opening thereof.

FIG. 22 III schematically shows a supra mitral device 50, having essentially a narrow anterior part 52, a posterior part 56 having an extension 54 between posterior part 56 and the opening of device 30; extension 54 is configured to cover (overlap with) the anterior mitral leaflet. Extension 54 may integrally be formed with posterior part 56. Extension 54 may integrally be contiguous with posterior part 56. Extension 54 may be connected to posterior part 56. Supra mitral device 50 has a varying stiffness (stiffness gradient) between an outer and an inner perimeter thereof. For example, the stiffness increases along an axis extending from an inner to an outer perimeter of device 50.

FIG. 22 IV schematically shows a supra mitral device 60, having essentially a narrow anterior part 62, a posterior part 66 having an extension 64 between posterior part 66 and the opening of device 60; extension 64 is configured to cover (overlap with) the anterior mitral leaflet. Extension 64 may integrally be formed with posterior part 66. Extension 64 may integrally be contiguous with posterior part 66. Extension 64 may be connected to posterior part 66. Device 60 further comprises an enforcement member 68 extending along an inner edge of the opening thereof. Supra mitral device 60 has a varying stiffness (stiffness gradient) between an outer and an inner perimeter thereof. For example, the stiffness increases along an axis extending from an inner to an outer perimeter of device 60.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What I claim is:

1. A supra mitral device for mitral/tricuspid valve repair in a subject in need thereof, the device comprising:
a main body portion having an essentially annular D-shape radially outer perimeter and an essentially annular D-shape opening, such that a posterior section of said main body portion is wider than an anterior section of said main body portion, said anterior and said posterior sections comprising a sheet of material and said posterior section is said posterior section configured for coverage and attachment to essentially a whole section of a posterior leaflet of a mitral valve, which faces a left atrium on systole, such that the posterior section of said main body portion is attached to said section of the posterior leaflet that faces the left atrium on systole, while assuming a shape of the posterior leaflet section, thereby preventing and/or reducing mitral regurgitation, without utilizing an implanted valve, leaving the posterior leaflet at least partially open and functional; wherein said posterior section of said main body portion is made of a pliable material, adapted to stiffen after implantation of the device, wherein an atrial facing surface of said device is planar, wherein an opposing ventricle facing surface of said device is planar, and wherein the atrial facing surface and the opposing ventricle facing surface are parallel.

2. The device of claim 1, wherein said posterior section of said main body portion is configured to stay attached/adherent/bonded to said section of the posterior leaflet which faces the left atrium on systole throughout a cardiac cycle, thereby maintaining/immobilizing the posterior leaflet at an essentially permanently elevated/closed position.

3. The device of claim 1, wherein said main body portion is not directly attached to an annulus of the mitral valve.

4. The device of claim 1, wherein the main body portion further comprises a plurality of through holes for securing said device to the mitral valve leaflet.

5. The device of claim 1, wherein the pliable material comprises felt and/or cloth.

6. The device of claim 5, wherein the felt comprises polytetrafluoroethylene (PTFE), polyethylene terephthalate (PET), expanded PTFE (ePTFE), or any combination thereof.

7. The device of claim 1, wherein the main body portion has a stiffness gradient between an outer and an inner perimeter thereof.

8. The device of claim 1, further comprising an enforcement element extending along an inner perimeter of said main body portion.

9. The device of claim 1, further comprising an enforcement element extending along at least a part of an inner perimeter of said main body portion configured to support a particular location of the posterior leaflet where a leak occurs.

10. The device of claim 1, wherein said posterior section of said main body portion is configured to extend beyond an area of the posterior leaflet and thus to overlap a portion of an anterior mitral leaflet, thereby preventing/reducing the mitral regurgitation.

11. The device of claim 1, wherein said main body portion further comprises an extension, contiguous with or attached to said posterior section and configured to extend beyond an area of the posterior leaflet and thus, when implanted, to overlap with a posterior part of an anterior leaflet, thereby preventing/reducing the mitral regurgitation.

12. The device of claim 11, wherein the extension is made of a less traumatic material than that of said posterior section.

13. The device of claim 1, configured for trans-catheter implantation.

14. The device of claim 1, wherein the subject suffers from mitral insufficiency.

15. The device of claim 14, wherein the mitral insufficiency comprises fibroelastic deficiency, myxomatous mitral valve, functional mitral regurgitation (FMR), or combinations thereof.

16. A method of percutaneous mitral valve repair, the method comprising attaching the device of claim 1, supra mitrally, to the posterior leaflet along its outer and inner margins, thus coupling the device to the entire posterior mitral leaflet section that faces the left atrium on systole, and to an anterior leaflet at its outer margins only, the posterior section of said main body portion is attached to said section of the posterior leaflet that faces the left atrium on systole, while assuming the shape of the posterior leaflet section, thus completing attachment of the main body portion to the circumference of the mitral valve, thereby preventing and/or reducing mitral regurgitation, without utilizing an implanted valve, leaving the posterior leaflet at least partially open and functional.

17. The method of claim 16, wherein attaching comprises using multiple coupling elements, wherein at least one of the coupling elements comprises a wire comprising a shape memory material configured to assume a spiral shape; wherein the spiral shape comprises a first spiral and a second spiral interconnected by an essentially straight wire; wherein a distal end of a first end forms an innermost loop of the first spiral, and a proximal end of the first end forms an outermost loop of the first spiral; and wherein a distal end of a second end forms an outermost loop of the second spiral and a proximal end of the second end forms an innermost loop of the second spiral.

18. The method of claim 16, further comprising a later second stage step, if residual mitral regurgitation is deemed unacceptable on follow-up, to exploit the device as a docking system for per-catheter mitral valve replacement.

19. A kit for percutaneous mitral valve repair or Replacement (PCMVR), the kit comprising:
the device of claim 1; and
a plurality of coupling elements configured to attach the main body portion to the posterior leaflet of the mitral valve.

* * * * *